United States Patent
Durairaj et al.

(10) Patent No.: US 7,365,113 B2
(45) Date of Patent: Apr. 29, 2008

(54) PHOSPHATE ESTER FLAME RETARDANTS FROM RESORCINOL-KETONE REACTION PRODUCTS

(76) Inventors: Raj B. Durairaj, 123 Edgemeade Dr., Monroeville, PA (US) 15146; Gary A. Jesionowski, 333 Haugh Dr., Pittsburgh, PA (US) 15237

( * ) Notice: Subject to any disclaimer, the term of this patent is extended or adjusted under 35 U.S.C. 154(b) by 196 days.

(21) Appl. No.: 11/233,586

(22) Filed: Sep. 21, 2005

(65) Prior Publication Data

US 2006/0063867 A1    Mar. 23, 2006

Related U.S. Application Data

(60) Provisional application No. 60/611,962, filed on Sep. 22, 2004.

(51) Int. Cl.
- *C08K 5/49* (2006.01)
- *C08K 5/521* (2006.01)
- *C09K 21/00* (2006.01)
- *C07F 9/02* (2006.01)

(52) U.S. Cl. ............ 524/110; 252/609; 549/201; 549/202; 549/336; 549/384; 549/406; 558/71; 558/77; 558/83; 558/87; 558/143; 558/210; 558/211

(58) Field of Classification Search ......... 252/609; 524/110; 549/201, 202, 336, 384, 406; 558/71, 558/77, 83, 87, 143, 210, 211
See application file for complete search history.

(56) References Cited

U.S. PATENT DOCUMENTS

| | | | |
|---|---|---|---|
| 5,204,394 A | 4/1993 | Gosens et al. | |
| 5,418,317 A | 5/1995 | Raymond | |
| 5,602,201 A | 2/1997 | Fujiguchi et al. | |
| 6,204,313 B1 | 3/2001 | Bastiaens et al. | |
| 6,465,548 B1 * | 10/2002 | Inoue et al. | 524/110 |
| 6,583,256 B2 | 6/2003 | Vollenberg et al. | |
| 7,083,743 B2 * | 8/2006 | Krohnke et al. | 252/400.24 |
| 2002/0111466 A1 * | 8/2002 | Hendler et al. | 536/8 |

FOREIGN PATENT DOCUMENTS

| | | |
|---|---|---|
| EP | 0509506 A2 | 10/1992 |
| JP | 63-210184 | 8/1988 |
| JP | 2002-138283 | 5/2002 |

OTHER PUBLICATIONS

Raj Durairaj, "Flame Retardant" in "Resorcinol: Chemistry, Technology and Applications," Springer Verlag Publisher, Chapter 8.2, pp. 592-631 (2005), Dec. 2005.

* cited by examiner

*Primary Examiner*—Kriellion A Sanders

(57) ABSTRACT

Flavan-based and spirodichroman compound-based phosphate esters prepared by reacting flavans and spirodichroman compounds with phosphorus oxychloride, monophenyl dichlorophosphate, or diphenyl chlorophosphate compounds are described. The flavans and spirodichroman compounds can be synthesized by the reaction of resorcinol with aliphatic acetone. Such phosphate esters can be used as flame retardants.

53 Claims, No Drawings

PHOSPHATE ESTER FLAME RETARDANTS FROM RESORCINOL-KETONE REACTION PRODUCTS

PRIOR RELATED APPLICATIONS

This application claims the benefit under 35 U.S.C. § 120 of U.S. Provisional Patent Application Ser. No. 60/611,962, filed Sep. 22, 2004, which is incorporated herein by reference in its entirety.

FIELD OF THE INVENTION

This invention relates to flame retardants comprising flavan-based and spirodichroman compound-based phosphate esters, methods for their synthesis and applications thereof, particularly their applications as flame retardants in compositions or articles comprising polymeric materials.

BACKGROUND OF THE INVENTION

Polymers such as plastics, elastomers, and thermosets are used in large volumes in a wide range of applications such as walls, ceilings, furniture, floor coverings, fabrics, electronics, vehicles and electrical appliances. Because most polymers are flammable, fire safety is important in each of these applications. Generally, fire safety of polymers can be improved by incorporating flame retardants into the polymers. Flame retardants consist of compounds added to a material to improve the material's ability to withstand fire and heat or to resist combustion. Flame retardants can function in a variety of ways to reduce the risk of fire hazard. In one way, they can raise the ignition temperature. In the other ways, they can reduce the rate of burning, flame spread, or the generation of toxic gases and smoke. Phosphorus flame retardants can reduce the flammability of the polymer and reduce the generation of toxic gases and smoke.

There are many different kinds of flame retardants which include alumina trihydrate, magnesium hydroxide, halogenated compounds (e.g., chlorinated, fluorinated and brominated compounds), phosphorus compounds (e.g., phosphate esters), antimony oxide, melamine derivatives, and boric acid and other boron compounds. The worldwide sale of flame retardants was 2.35 billion pounds in 2003. It is predicted that the worldwide sale of flame retardants will increase to 2.82 billion pounds in 2008. Among all flame retardants, the two most common kinds are phosphorus flame retardants and halogenated flame retardants. Because of environmental and health concerns over halogenated flame retardants, many parts of Europe are considering bans on some specific halogenated flame retardants. Therefore, the trend is to restrain the use of the halogenated flame retardants and to migrate to other flame retardants such as phosphorus flame retardants. Some examples of phosphorus flame retardants currently in the market includes phosphate ester type flame retardants such as resorcinol bis(diphenyl phosphate) (RDP), bisphenol A bis(diphenyl phosphate), monomeric aromatic phosphate ester compounds (e.g., triphenyl phosphate and tricresyl phosphate) and the like. In general, resorcinol-based phosphate ester flame retardants such as RDP have some more desirable properties over the bisphenol A-based phosphate ester flame retardants because of the presence of meta-phenylene linkages in the former.

Some well known polymers, such as polycarbonates (PC) and polyphenylene oxide (PPO), have a wide range of industrial applications. In order to improve their impact strength properties, they are often blended with acrylonitrile-butadiene-styrene terpolymer (ABS) and high-impact polystyrene (HIPS). Since ABS and HIPS polymers are mainly hydrocarbon-based materials, they generally have a tendency to burn in the case of accidental fire. Though halogenated flame retardants are widely used with ABS and HIPS polymers, the phosphate ester type flame retardants are proven to be suitable for the PC/ABS and PPO/HIPS blends. It has been well known that resorcinol-based phosphate esters, such as RDP, are widely used in PC/ABS and PPO/HIPS blends as flame retardants. RDP can improve the melt flow properties and processability properties and enhance the char forming characteristics of the PC/ABS and PPO/HIPS blends. Similarly, other resorcinol-based phosphate ester flame retardants may also improve melt flow properties and processability properties of polymers while reducing the flammability of the polymers.

Generally, the flame retardants used in PC/ABS and PPO/HIPS blends are primarily aromatic phosphate esters based on resorcinol and bisphenol-A. Although these flame retardants can provide adequate flame retarding and other mechanical properties to PC/ABS and PPO/HIPS, there are always needs for improved flame retardants that can provide better melt flow and heat distortion performances than the resorcinol and bisphenol-A phosphate esters. Disclosed herein are new flame retardants that can meet the above-mentioned needs.

SUMMARY OF THE INVENTION

Disclosed herein are new flame retardants that have desirable flame retarding, melt flow and heat distortion performances.

In one aspect, the flame retardants comprise at least a phosphate ester compound having the formula:

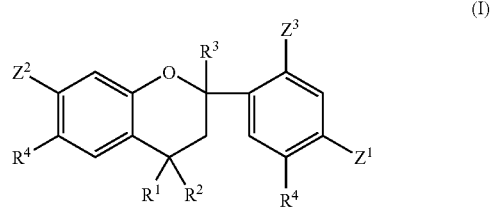

(I)

wherein each of $Z^1$, $Z^2$, and $Z^3$ is independently —OH or a phosphate ester group; and each of $R^1$, $R^2$, $R^3$, and $R^4$ is independently H, alkyl, alkenyl, alkynyl, heteroalkyl, aryl, heteroaryl, cycolalkyl, and heterocycloalkyl.

In some embodiments, the phosphate ester group has the formula:

(II)

wherein each of $R^5$ and $R^6$ is independently alkyl, alkenyl, alkynyl, heteroalkyl, aryl, heteroaryl, cycloalkyl, or heterocycloalkyl, or a part of a heterocyclic group when $R^5$ and $R^6$ form the heterocyclic group together with the —O—P(=O)(—O—)—O— fragment; and where each alkyl, alkenyl, alkynyl, heteroalkyl, aryl, heteroaryl, cycloalkyl, and heterocycloalkyl group is substituted or unsubstituted.

In another aspect, the flame retardants comprise at least a phosphate ester compound having the formula:

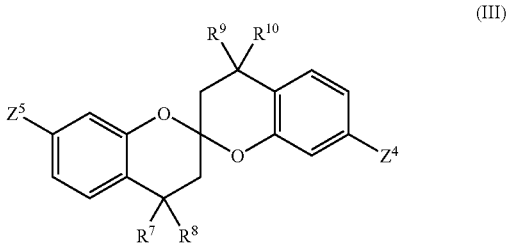

(III)

wherein each of $Z^4$ and $Z^5$ is a phosphate ester group; and each of $R^7$, $R^8$, $R^9$, and $R^{10}$ is independently H, alkyl, alkenyl, alkynyl, heteroalkyl, aryl, heteroaryl, cycolalkyl, and heterocycloalkyl.

Disclosed herein are also new processes of making flame retardants that have desirable flame retarding, melt flow and heat distortion performances.

In one aspect, the process of preparing the flame retardant of Formula (I) comprises the step of reacting a resorcinol flavan compound having the formula:

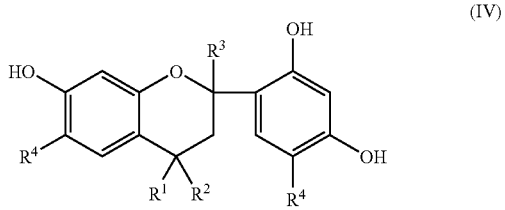

(IV)

with at least a chlorophosphate compound having the formula:

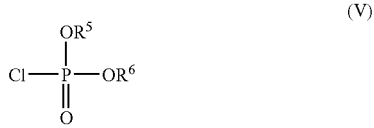

(V)

in the presence of a catalyst or an acid acceptor,
  wherein each of $Z^1$, $Z^2$, and $Z^3$ is independently —OH or a phosphate ester group; and each of $R^1$, $R^2$, $R^3$, and $R^4$ is independently H, alkyl, alkenyl, alkynyl, heteroalkyl, aryl, heteroaryl, cycolalkyl, and heterocycloalkyl;
  each of $R^5$ and $R^6$ is independently alkyl, alkenyl, alkynyl, heteroalkyl, aryl, heteroaryl, cycloalkyl, or heterocycloalkyl, or a part of a heterocyclic group when $R^1$ and $R^2$ form the heterocyclic group together with the —O—P(=O)(—Cl)—O— fragment; and
  where each alkyl, alkenyl, alkynyl, heteroalkyl, aryl, heteroaryl, cycloalkyl, and heterocycloalkyl group is substituted or unsubstituted.

In another aspect, the process of preparing the flame retardant of Formula (III) comprises the step of reacting a resorcinol spirodichroman compound having the formula:

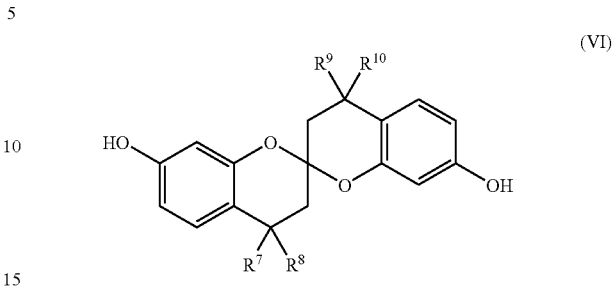

(VI)

with at least a chlorophosphate compound having the formula:

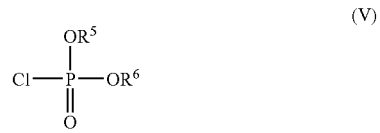

(V)

in the presence of a catalyst or an acid acceptor,
  wherein each of $Z^4$ and $Z^5$ is a phosphate ester group; and each of $R^7$, $R^8$, $R^9$, and $R^{10}$ is H, alkyl, alkenyl, alkynyl, heteroalkyl, aryl, heteroaryl, cycolalkyl, and heterocycloalkyl;
  each of $R^5$ and $R^6$ is independently alkyl, alkenyl, alkynyl, heteroalkyl, aryl, heteroaryl, cycloalkyl, or heterocycloalkyl, or a part of a heterocyclic group when $R^1$ and $R^2$ form the heterocyclic group together with the —O—P(=O)(—Cl)—O— fragment; and
  where each alkyl, alkenyl, alkynyl, heteroalkyl, aryl, heteroaryl, cycloalkyl, and heterocycloalkyl group is substituted or unsubstituted.

In another aspect, the process of preparing the flame retardant of Formula (I) where the phosphate ester group is represented by Formula (II) comprises the step of reacting a compound of the formula:

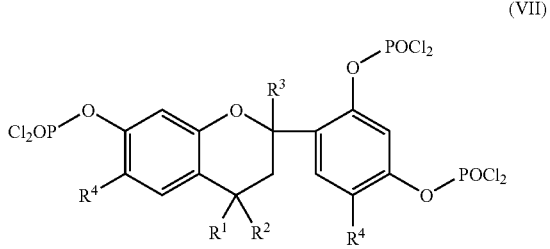

(VII)

with at least one hydroxyl compound in the presence of a catalyst.

In another aspect, the process of preparing the flame retardant of Formula (III) where the phosphate ester group is represented by Formula (II) comprises the step of reacting a compound of the formula:

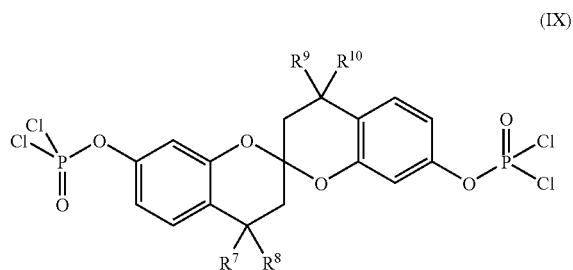

(IX)

with at least one hydroxyl compound in the presence of a catalyst.

Disclosed herein are also new flame retardant compositions comprising a polymer and a flame retardant of Formula (I) or Formula (III) and articles comprising the flame retardant compositions.

DESCRIPTION OF EMBODIMENTS OF THE INVENTION

In the following description, all numbers disclosed herein are approximate values, regardless whether the word "about" or "approximate" is used in connection therewith. They may vary by 1 percent, 2 percent, 5 percent, or, sometimes, 10 to 20 percent.

Whenever a numerical range with a lower limit, $R^L$ and an upper limit, $R^U$, is disclosed, any number falling within the range is specifically disclosed. In particular, the following numbers within the range are specifically disclosed: $R=R^L+k*(R^U-R^L)$, wherein k is a variable ranging from 1 percent to 100 percent with a 1 percent increment, i.e., k is 1 percent, 2 percent, 3 percent, 4 percent, 5 percent, . . . , 50 percent, 51 percent, 52 percent, . . . , 95 percent, 96 percent, 97 percent, 98 percent, 99 percent, or 100 percent. Moreover, any numerical range defined by two R numbers as defined in the above is also specifically disclosed.

Embodiments of the invention provide new flavan-based and spirodichroman compound-based phosphate esters which can function as flame retardants in compositions or articles comprising polymeric materials such as polycarbonates (PC), poly(phenylene oxide) (PPO), polyesters (e.g., PET and PBT), polycarbonate and acrylonitrile-butadiene-styrene terpolymer (PC/ABS) blends, poly(phenylene oxide) and high-impact polystyrene (PPO/HIPS) blends, and other polymers. Such new flavan-based and spirodichroman compound-based phosphate esters can be used as flame retardants in plastics and other polymeric systems and can improve their flow properties. These new flame retardants may possess enhanced melt flow properties and processability properties compared to resorcinol-based phosphate esters such as diphosphate ester resorcinol (RDP). Synthetic procedures to prepare flavan-based and spirodichroman compound-based phosphate esters are also provided.

The phosphate ester compounds disclosed herein are novel, and have the potential to be used as effective and efficient flame retardants in various industrial applications.

In one embodiment, this invention provides a flame retardant comprising at least a phosphate ester compound having the formula:

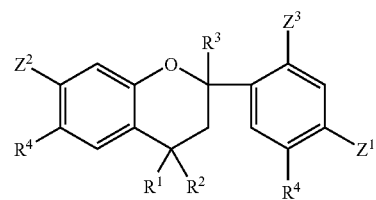

(I)

wherein each of $Z^1$, $Z^2$, and $Z^3$ is independently —OH or a phosphate ester group; and each of $R^1$, $R^2$, $R^3$, and $R^4$ is independently H, alkyl, alkenyl, alkynyl, heteroalkyl, aryl, heteroaryl, cycloalkyl, and heterocycloalkyl.

In another embodiment, the invention provides a flame retardant comprising at least a phosphate ester compound having the formula:

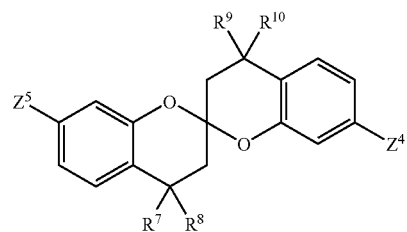

(III)

wherein each of $Z^4$ and $Z^5$ is a phosphate ester group; and each of $R^7$, $R^8$, $R^9$, and $R^{10}$ is independently H, alkyl, alkenyl, alkynyl, heteroalkyl, aryl, heteroaryl, cycloalkyl, and heterocycloalkyl.

Each phosphate ester group in compounds of Formula (I) and (III) have the formula:

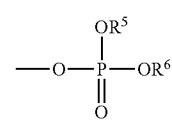

(II)

wherein each of $R^5$ and $R^6$ is independently alkyl, alkenyl, alkynyl, heteroalkyl, aryl, heteroaryl, cycloalkyl, or heterocycloalkyl, or a part of a heterocyclic group when $R^5$ and $R^6$ form the heterocyclic group together with the —O—P(═O)(—O—)—O— fragment; and where each alkyl, alkenyl, alkynyl, heteroalkyl, aryl, heteroaryl, cycloalkyl, and heterocycloalkyl group is substituted or unsubstituted. Non-limiting examples of the substituted alkyl group include aralkyls such as 4-(nitrophenyl)ethyl. Non-limiting examples of the substituted aryl group include halogenated aryls such as 2,4-dichlorophenyl and alkylated aryls such as, 2-methylphenyl, 4-methylphenyl, and 3,5-dimethylphenyl.

In some embodiments, each of $R^5$ and $R^6$ in the compound of Formula (II) is independently a part of a heterocyclic group when $R^5$ and $R^6$ form a heterocyclic group together with the —O—P(═O)(—O—)—O— fragment. The heterocyclic group may be substituted or unsubstituted. Non-limiting examples of such heterocyclic group include the following formulae:

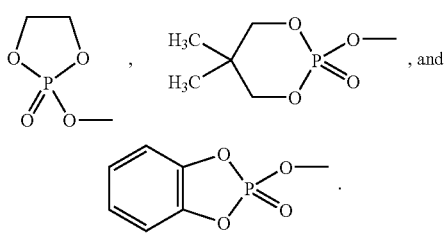

In some embodiments, each of $R^5$ and $R^6$ is independently aryl. In a particular embodiment, each of $R^5$ and $R^6$ is independently phenyl. In other embodiments, the phosphate ester group is selected from the group consisting of radicals having the following formulae:

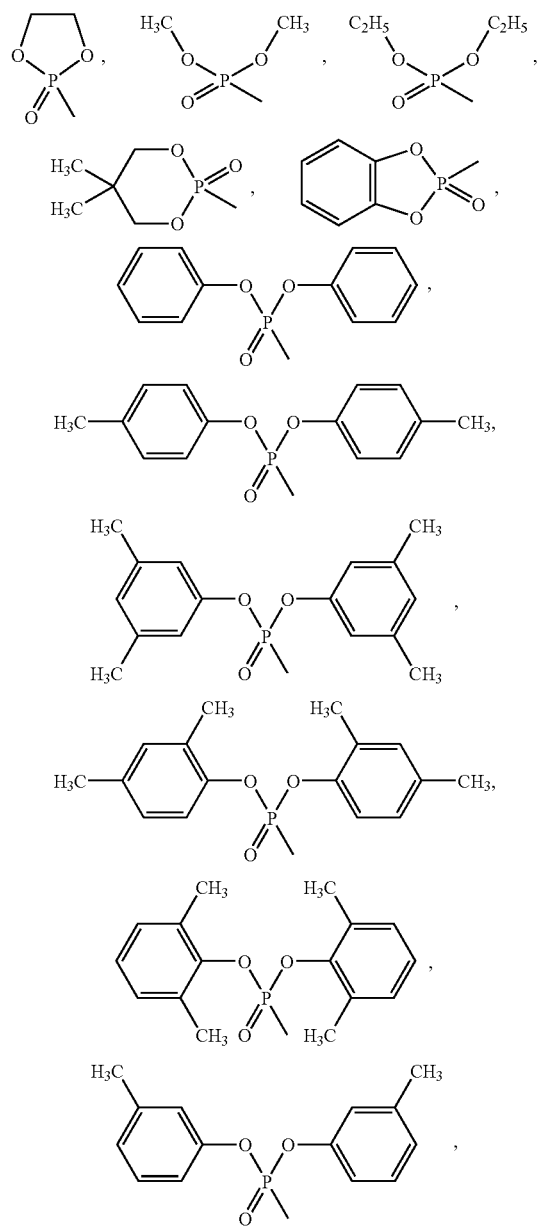

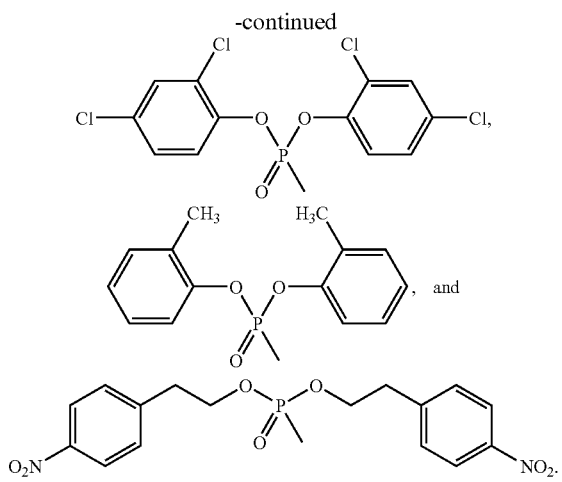

-continued

As used herein and unless otherwise indicated, the term "alkyl" or "alkyl group" means a univalent group having the general formula $C_nH_{2n+1}$ derived from removing a hydrogen atom from a saturated, unbranched or branched aliphatic hydrocarbon, where n is an integer, preferably between 1 and 20, more preferably between 1 and 8. Examples of alkyl groups include, but are not limited to, $(C_1-C_8)$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl and octyl. Longer alkyl groups include nonyl and decyl groups. An alkyl group can be unsubstituted or substituted with one or more suitable substituents. Furthermore, the alkyl group can be branched or unbranched.

As used herein and unless otherwise indicated, the term "heteroalkyl" or "heteroalkyl group" means a univalent group derived from an alkyl group with at least one of the methylene group is replaced by a heteroatom or a heterogroup such as O, S, or NR where R is H or an organic group.

As used herein and unless otherwise indicated, the term "cycloalkyl" or "cycloalkyl group" means a univalent group derived from a cycloalkane by removal of a hydrogen atom from a non-aromatic, monocyclic or polycyclic ring comprising carbon and hydrogen atoms. Examples of cycloalkyl groups include, but are not limited to, $(C_3-C_7)$ cycloalkyl groups, such as cyclopropyl, cyclobutyl, cyclopentyl, cyclohexyl, and cycloheptyl, and saturated cyclic and bicyclic terpenes and $(C_3-C_7)$cycloalkenyl groups, such as cyclopropenyl, cyclobutenyl, cyclopentenyl, cyclohexenyl, and cycloheptenyl, and unsaturated cyclic and bicyclic terpenes. A cycloalkyl group can be unsubstituted or substituted by one or two suitable substituents. Furthermore, the cycloalkyl group can be monocyclic or polycyclic.

As used herein and unless otherwise indicated, the term "heterocycloalkyl" or "heterocycloalkyl group" means a univalent group derived from a monocyclic or polycyclic heterocycloalkane by removal of a hydrogen atom from a ring carbon atom. Non-limiting examples of the heterocycloalkyl group include oxirane, thiirane, aziridine, oxetane, thietane, azetidine, pyrrolidine, tetrahydrothiophene, tetrahydrofuran, 2-pyrrolidinone, 2,5-pyrrolidinedione, dihydro-2(3H)-furanone, dihydro-2,5-furandione, dihydro-2

(3H)-thiophenone, 3-aminodihydro-2(3H)-thiophenone, piperidine, 2-piperidinone, 2,6-piperidinedione, tetrahydro-2H-pyran, tetrahydro-2H-pyran-2-one, dihydro-2H-pyran-2,6(3H)-dione, and tetrahydro-4H-thiopyran-4-one. A heterocycloalkyl group can be unsubstituted or substituted with one or more suitable substituents. Furthermore, the heterocycloalkyl group can be monocyclic or polycyclic.

As used herein and unless otherwise indicated, the term "aryl" or "aryl group" means an organic radical derived from a monocyclic or polycyclic aromatic hydrocarbon by removing a hydrogen atom. Non-limiting examples of the aryl group include phenyl, naphthyl, benzyl, or tolanyl group, sexiphenylene, phenanthrenyl, anthracenyl, coronenyl, and tolanylphenyl. An aryl group can be unsubstituted or substituted with one or more suitable substituents. Furthermore, the aryl group can be monocyclic or polycyclic.

As used herein and unless otherwise indicated, the term "heteroaryl" or "heteroaryl group" means an organic radical derived from a monocyclic or polycyclic aromatic heterocycle by removing a hydrogen atom. Non-limiting examples of the heteroaryl group include furyl, thienyl, pyrrolyl, indolyl, indolizinyl, isoindolyl, pyrazolyl, imidazolyl, thiazolyl, thiadiazolyl, benzothiazolyl, 1,2,4-triazolyl, 1,2,3-triazolyl, indazolyl, benzotriazolyl, benzimidazolyl, indazolyl carbazolyl, carbolinyl, benzofuranyl, isobenzofuranyl benzothiophenyl, dibenzofuranyl, dibenzothiophenyl, isothiazolyl, isoxazolyl, pyridyl, purinyl, pyridazinyl, pyrimidinyl, pyrazinyl, triazinyl, tetrazinyl, petazinyl, quinolinyl, isoquinolinyl, perimidinyl, cinnolinyl, phthalazinyl, quinazolinyl, quinoxalinyl, naphthyridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4)dioxinyl, and thianthrenyl. A heteroaryl group can be unsubstituted or substituted with one or more suitable substituents. Furthermore, the heteroaryl group can be monocyclic or polycyclic.

As used herein and unless otherwise indicated, the term "alkenyl" or "alkenyl group" means a monovalent, unbranched or branched hydrocarbon chain having one or more double bonds therein. The double bond of an alkenyl group can be unconjugated or conjugated to another unsaturated group. Suitable alkenyl groups include, but are not limited to ($C_2$-$C_8$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-butenyl)-pentenyl. An alkenyl group can be unsubstituted or substituted with one or two suitable substituents. Furthermore, the alkenyl group can be branched or unbranched.

As used herein and unless otherwise indicated, the term "alkynyl" or "alkynyl group" means monovalent, unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_8$) alkynyl groups, such as ethynyl, propynyl, butynyl, pentynyl, hexynyl, methylpropynyl, 4-methyl-1-butynyl, 4-propyl-2-pentynyl, and 4-butyl-2-hexynyl. An alkynyl group can be unsubstituted or substituted with one or two suitable substituents. Furthermore, the alkynyl group can be branched or unbranched.

As used herein and unless otherwise indicated, the term "heterocyclic" or "heterocyclic group" means any monocyclic or polycyclic (e.g., bicyclic, tricyclic, etc.) ring compound having at least a heteroatom (e.g., O, S, N, P, B, Si, etc.) in the ring. The heterocyclic group may be aromatic or non-aromatic.

As used herein and unless otherwise indicated, the term "substituted" as used to describe a compound or chemical moiety means that at least one hydrogen atom of that compound or chemical moiety is replaced with a second chemical moiety. The second chemical moiety can be any desired substituent that does not adversely affect the desired activity of the compound. Examples of substituents are those found in the exemplary compounds and embodiments disclosed herein, as well as halogen; alkyl; heteroalkyl; alkenyl; alkynyl; aryl; heteroaryl; hydroxyl; alkoxyl; amino; nitro; thiol; thioether; imine; cyano; amido; phosphonato; phosphine; carboxyl; thiocarbonyl; sulfonyl; sulfonamide; ketone; aldehyde; ester; oxo; haloalkyl (e.g., trifluoromethyl); carbocyclic cycloalkyl, which can be monocyclic or fused or non-fused polycyclic (e.g., cyclopropyl, cyclobutyl, cyclopentyl or cyclohexyl) or a heterocycloalkyl, which can be monocyclic or fused or non-fused polycyclic (e.g., pyrrolidinyl, piperidinyl, piperazinyl, morpholinyl or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl or benzofuranyl); amino (primary, secondary or tertiary); —O-lower alkyl; —O-aryl, aryl; aryl-lower alkyl; —$CO_2CH_3$; —$CONH_2$; —$OCH_2CONH_2$; —$NH2$; —$SO_2NH_2$; —$OCHF_2$; —$CF_3$; —$OCF_3$; —NH(alkyl); —N(alkyl)$_2$; —NH(aryl); —N(alkyl)(aryl); —N(aryl)$_2$; —CHO; —CO(alkyl); —CO(aryl); —$CO_2$(alkyl); and —$CO_2$(aryl); and such moieties can also be optionally substituted by a fused-ring structure or bridge, for example —$OCH_2O$—. These substituents can optionally be further substituted with a substituent selected from such groups. All chemical groups disclosed herein can be substituted, unless it is specified otherwise.

Flame retardant compositions having improved flammability characteristics can be formulated by adding at least a flame retardant of Formula (I) to at least a polymer. Non-limiting examples of polymers include polycarbonates (PC), poly(phenylene oxide) (PPO), polyesters (e.g., PET and PBT), acrylonitrile-butadiene-styrene terpolymer (ABS), high-impact polystyrene (HIPS), polyarylates, and combinations or blends thereof such as the polycarbonate and acrylonitrile-butadiene-styrene terpolymer (PC/ABS) blend and the poly(phenylene oxide) and high-impact polystyrene (PPO/HIPS) blend. In some embodiments, the flame retardant compositions further comprise at least a second flame retardant known in the art such as phosphate esters (e.g., RDP), alumina trihydrate, magnesium hydroxide, halogenated compounds, antimony oxide, melamine derivatives, and boric acid and other boron compounds. In other embodiments, the flame retardant compositions are substantially free of a second flame retardant known in the art, which can be selected from the group consisting of phosphate esters, alumina trihydrate, magnesium hydroxide, halogenated compounds, antimony oxide, melamine derivatives, boric acid and other boron compounds, and combinations thereof. As used herein and unless otherwise indicated, a composition that is "substantially free" of a compound or an additive means that the composition contains less than about 20% by weight, more preferably less than about 10% by weight, even more preferably less than about 5% by weight, and most preferably less than about 3% by weight of the compound or the additive.

Optionally, the flame retardant compositions can further comprise at least one additive such as extenders, fibers, fillers, coupling agents, cross-linking agents, plasticizers, impact modifiers, compatibilizers, anti-blocking agents, anti-fogging agents, anti-aging agents, antioxidants, UV stabilizers, antiozonants, acid scavengers, processing aids, surfactants, lubricants, plasticizing agents, parting agents and abherents, nucleating agents, anti-static agents, slip agents, chemical blowing agents, fluorescent whitening agents, flow agents, deodorants, release agents, colorants such as dye and pigments, and anti-microbials such as bactericides. Some of the above-mentioned additives are described in Zweifel, et al., "*Plastics Additives Handbook*," Hanser Gardner Publications, Cincinnati, Ohio, 5th edition (2001); John Murphy, "*Additives for Plastics Handbook*," Elsevier Science Pub. Co., New York, N.Y., 2nd edition (2001), both of which are incorporated herein by reference in their entirety. In some embodiments, the flame retardant compositions are substantially free of an additive.

The flame retardant compositions can be used to prepare articles by known polymer processes such as extrusion, injection molding, rotational molding, and molding. In general, extrusion is a process by which a polymer is propelled continuously along a screw through regions of high temperature and pressure where it is melted and compacted, and finally forced through a die. The extrusion of polymers is described in C. Rauwendaal, "*Polymer Extrusion*", Hanser Publishers, New York, N.Y. (1986); and M. J. Stevens, "*Extruder Principals and Operation*," Ellsevier Applied Science Publishers, New York, N.Y. (1985), both of which are incorporated herein by reference in their entirety.

Injection molding is also widely used for manufacturing a variety of plastic parts for various applications. In general, injection molding is a process by which a polymer is melted and injected at high pressure into a mold, which is the inverse of the desired shape, to form parts of the desired shape and size. The mold can be made from metal, such as steel and aluminum. The injection molding of polymers is described in Beaumont et al., "*Successful Injection Molding: Process, Design, and Simulation*," Hanser Gardner Publications, Cincinnati, Ohio (2002), which is incorporated herein by reference in its entirety.

Molding is generally a process by which a polymer is melted and led into a mold, which is the inverse of the desired shape, to form parts of the desired shape and size. Molding can be pressureless or pressure-assisted. The molding of polymers is described in Hans-Georg Elias "*An Introduction to Plastics*," Wiley-VCH, Weinhei, Germany, pp. 161-165 (2003), which is incorporated herein by reference.

Rotational molding is a process generally used for producing hollow plastic products. By using additional post-molding operations, complex components can be produced as effectively as other molding and extrusion techniques. Rotational molding differs from other processing methods in that the heating, melting, shaping, and cooling stages all occur after the polymer is placed in the mold, therefore no external pressure is applied during forming. The rotational molding of polymers is described in Glenn Beall, "*Rotational Molding: Design, Materials & Processing*," Hanser Gardner Publications, Cincinnati, Ohio (1998), which is incorporated herein by reference in its entirety.

In general, any article that comprises a polymer can be obtained with a flame retardant composition which contains the polymer and at least a flame retardant of Formula (I). Non-limiting examples of useful articles include plastic products, textiles, wood and paper products, adhesives and sealants, and rubber products, aerospace parts, automotive parts, wires, cables, construction materials, materials for interiors and furnishings, appliances, electronic components, computers, and business machines. In some embodiments, the articles are prepared by extrusion of the flame retardant composition. In other embodiments, the articles are prepared by injection molding of the flame retardant composition. In further embodiments, the articles are prepared by molding of the flame retardant composition. In additional embodiments, the articles are prepared by rotational molding of the flame retardant composition.

In one embodiment, the flame retardant having Formula (I) can be obtained or obtainable by reacting a resorcinol flavan compound having the formula:

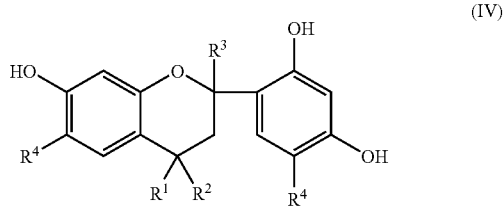

(IV)

with at least a chlorophosphate compound having the formula:

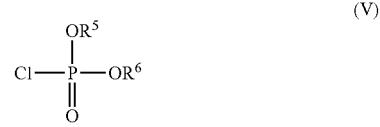

(V)

in the presence of a catalyst or an acid acceptor,
wherein each of $R^1$, $R^2$, $R^3$, and $R^4$ is independently H, alkyl or aryl;
each of $R^5$ and $R^6$ is independently alkyl, alkenyl, alkynyl, heteroalkyl, aryl, heteroaryl, cycloalkyl, or heterocycloalkyl, or a part of a heterocyclic group when $R^5$ and $R^6$ form the heterocyclic group together with the —O—P(=O)(—Cl)—O— fragment; and
where each of alkyl, alkenyl, alkynyl, heteroalkyl, aryl, heteroaryl, cycloalkyl, and heterocycloalkyl group is substituted or unsubstituted.

In another embodiment, the flame retardant having Formula (III) can be obtained by reacting by reacting a resorcinol spirodichroman compound having the formula:

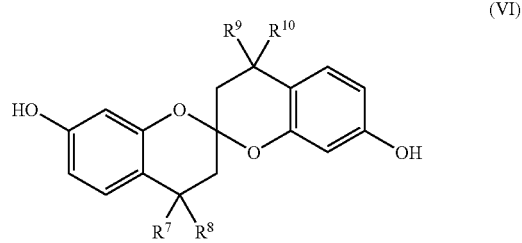

(VI)

with at least a chlorophosphate compound having the formula:

(V)

in the presence of a catalyst or an acid acceptor,
wherein each of $R^7$, $R^8$, $R^9$, and $R^{10}$ is independently H, alkyl, alkenyl, alkynyl, heteroalkyl, aryl, heteroaryl, cycolalkyl, and heterocycloalkyl;

each of $R^5$ and $R^6$ is independently alkyl, alkenyl, alkynyl, heteroalkyl, aryl, heteroaryl, cycloalkyl, or heterocycloalkyl, or a part of a heterocyclic group when $R^1$ and $R^2$ form the heterocyclic group together with the —O—P(=O)(—Cl)—O— fragment; and where each alkyl, alkenyl, alkynyl, heteroalkyl, aryl, heteroaryl, cycloalkyl, and heterocycloalkyl group is substituted or unsubstituted.

As used herein and unless otherwise indicated, the term "reacting" or the like means contacting one reactant, reagent, solvent, catalyst, reactive group or the like with another reactant, reagent, solvent, catalyst, reactive group or the like. Reactants, reagents, solvents, catalysts, reactive group or the like can be added individually, simultaneously or separately and can be added in any order. They can be added in the presence or absence of heat and can optionally be added under an inert atmosphere. "Reacting" can refer to in situ formation or intramolecular reaction where the reactive groups are in the same molecule.

The phosphorylation of the compound of Formula (IV) or Formula (VI) with a compound of Formula (V) can be promoted by either a catalyst such as magnesium chloride or an acid acceptor. The phosphorylation can occur in a solvent, preferably an inert organic solvent which does not react with the chloro group of the compound of Formula (V). Non-limiting examples of suitable inert organic solvents include aromatic hydrocarbons (e.g., toluene, benzene, and xylene), methylene chloride, chloroform, acetonitrile, ethers, ketones, dimethylformamide, trichloroethane, tetrahydrofuran, tetrachloroethylene, chlorobenzene and combinations thereof. In some embodiments, the solvent is toluene or methylene chloride.

Any phosphorylation catalyst known by a person of ordinary skill in the art can be used for the reaction between Formula (IV) or Formula (VI) and Formula (V). Non-limiting examples of phosphorylation catalysts include magnesium chloride, aluminum trichloride, titanium tetrachloride, and zinc dichloride. In some embodiments, the solvent for the magnesium chloride-catalyzed phosphorylation is toluene and the reaction temperature is greater than about 35° C., preferably greater than about 55° C., more preferably greater than about 75° C., and most preferably greater than about 100° C. The reaction product can be purified by washing the reaction mixture after completion with water or a basic aqueous solution such as sodium hydroxide solution, sodium carbonate solution, sodium bicarbonate solution, or potassium hydroxide solution. The amount of the catalyst can be in the range from 0.1 wt % to 10 wt % based on the total weight of the reactants. The reaction temperature can be greater than 25° C., greater than 50° C., greater than 75° C., greater than 100° C., greater than 120° C., greater than 140° C., or greater than 150° C.

Any compound that can neutralize hydrogen chloride can be used for the reaction between Formula (IV) or Formula (VI) and Formula (V). The acid acceptor can be an organic base. Non-limiting examples of suitable organic bases include amines (e.g., trimethylamine, triethylamine, N,N-diisopropylethylamine, triphenylamine, 1,8-diazabicyclo[5.4.0]undec-7-ene), 1-alkylpiperidines such as 1-ethylpiperidine, 1-alkylpyrrolidines such as 1-methylpyrrolidine, pyridine, and combinations thereof. Other suitable amines include, but not limited to, trialkylamines such as tributylamine, trioctylamine, trinonylamine, tridecylamine, triundecylamine, tridodecylamine, tri(tridecyl)amine, tripentadecylamine, trihexadecylamine, triheptadecylamine, trioctadecylamine, trinonadeclyamine, trieicosylamine, tri(tetrachlorododecyl)amine, trihexachloroheptadecylamine, lower alkyl substituted derivatives of pyridine (such as 2,6-lutidine and 2,4,6-collidine), 2,2,6,6-N-pentamethylpiperidine, N,N-dimethylaniline, and diisopropyl-N-ethylamine or combinations thereof. In some embodiments, the acid acceptor is triethylamine. In other embodiments, the solvent for the triethylamine-promoted phosphorylation is methylene chloride and the reaction temperature is less than about 50° C., preferably less than about 35° C., and more preferably between about 20° C. and about 25° C. The amount of the acid acceptor can be in the range from 1.0 to 1.5 mole per mole of chlorophosphate of Formula (V).

The mole ratio of the chlorophosphate of Formula (V) to the compound of Formula (VI) can be greater than about 10:1, greater than about 8:1, greater than about 6:1, greater than about 5:1, greater than about 4:1, greater than about 3:1, or greater than or equal to 2:1. In a particular embodiment, the mole ratio of the chlorophosphate of Formula (V) to the compound of Formula (VI) is greater than or equal to 2:1. The mole ratio of the chlorophosphate of Formula (V) to the compound of Formula (IV) can be greater than about 10:1, greater than about 8:1, greater than about 6:1, greater than about 5:1, greater than about 4:1, or greater than or equal to about 3:1. In a particular embodiment, the mole ratio of the chlorophosphate of Formula (V) to the compound of Formula (IV) can be greater than or equal to 3:1. In some embodiments where an excess of the compounds of Formula (IV), Formula (VI) or the chlorophosphate of Formula (V) is used, the excess unreacted reactant can be extracted or separated out with a combination of water and/or an aqueous basic solution and/or an acidic solution.

The chlorophosphate of Formula (V) can be any chlorophosphate that can react with the aromatic hydroxyl groups of the compound of Formula (IV) or Formula (VI). Non-limiting examples of suitable chlorophosphates of Formula (V) include 2-chloro-2-oxo-1,3,2-dioxaphospholane, dimethyl chlorophosphate, diethyl chlorophosphate, 2-chloro-5,5dimethyl-1,3,2-dioxaphophorinane-2-oxide, o-phenylene phosphorochloridate, diphenyl chlorophosphate, bis(2-methylphenyl) chlorophosphate, bis(4-methylphenyl) chlorophosphate, bis(3,5-dimethylphenyl) chlorophosphate, bis(2,6-dimethylphenyl) chlorophosphate, bis(2,4-dichlorophenyl) chlorophosphate, and bis[2-(4-nitrophenyl)ethyl] chlorophosphate, all of which are available from a commercial supplier such as Aldrich Chemicals, Milwaukee, Wis. In a particular embodiment, the chlorophosphate of Formula (V) is diphenyl chlorophosphate.

Alternatively, the compound of Formula (I) can be obtained by reacting a compound of the formula:

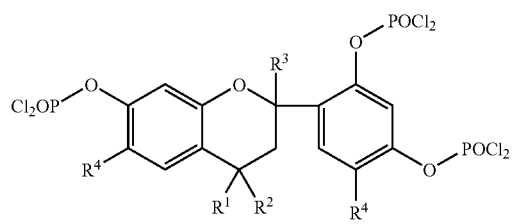

(VII)

with at least one hydroxyl compound in the presence of a catalyst.

Similarly, the compound of Formula (III) can be obtained by reacting a compound of the formula:

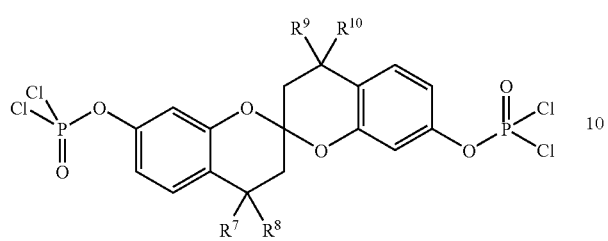

(IX)

with at least one hydroxyl compound in the presence of a catalyst.

The hydroxyl compound for the preparation of Formula (I) or Formula (III) can be a mono-hydroxyl compound or a polyol such as diols, triols, tetrols, etc. In some embodiments, the hydroxyl compound is a mono-hydroxyl compound. Non-limiting examples of suitable mono-hydroxyl compounds include mono-hydroxyl aromatic alcohols such as phenol, 2-methylphenol, 4-methylphenol, 3,5-dimethylphenol, 2,4-dichlorophenol, and mono-hydroxyl aliphatic alcohols such as 2-(4-nitrophenyl)ethanol, methanol, and ethanol, all of which can be obtained from a commercial supplier such as Aldrich Chemicals, Milwaukee, Wis. The mole ratio of the mono-hydroxyl compound to the compound of Formula (VII) can be greater than about 1000:1, greater than about 100:1, greater than about 10:1, greater than about 9:1, greater than about 8:1, greater than about 7:1, or greater than or equal to 6:1. The mole ratio of the mono-hydroxyl compound to the compound of the Formula (IX) can be can be greater than about 1000:1, greater than about 100:1, greater than about 10:1, greater than about 9:1, greater than about 8:1, greater than about 7:1, greater than about 6:1, greater than about 5:1, or greater than or equal to 4:1.

In other embodiments, the hydroxyl compound for the preparation of Formula (I) or Formula (III) is a diol. The diol can react with the chlorophosphate groups of the compound of Formula (VII) or the Formula (IX) to form heterocyclic rings containing the —O—P(=O)(—O—)—O— fragment. Non-limiting examples of suitable diols include 1,2-dihydroxybenzene, 4-methyl-1,2-benzenediol, 3-methyl-1,2-benzenediol, 3-fluoro-1,2-benzenediol, 4-chloro-1,2-benzenediol, 3,4-dihydroxybenzonitrile, 3,4-dihydroxybenzaldehyde, 3-methoxy-1,2-benzenediol, 1,3-propanediol, 2,2-dimethyl-1,3-propanediol, 2-ethyl-2-methyl-1,3-propanediol, and ethylene glycol, all of which can be obtained from a commercial supplier such as Aldrich Chemicals, Milwaukee, Wis. The mole ratio of the diol to the compound of Formula (VII) can be greater than about 1000:1, greater than about 100:1, greater than about 10:1, greater than about 9:1, greater than about 8:1, greater than about 7:1, greater than about 6:1, greater than about 5:1, greater than about 4:1, or greater than or equal to 3:1. The mole ratio of the diol to the compound of Formula (IX) can be greater than about 1000:1, greater than about 100:1, greater than about 10:1, greater than about 9:1, greater than about 8:1, greater than about 7:1, greater than about 6:1, greater than about 5:1, greater than about 4:1, greater than about 3:1, or greater than or equal to 2:1.

The compound of Formula (VII) can be obtained by reacting the resorcinol flavan compound of Formula (IV):

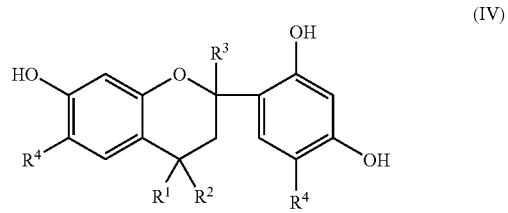

(IV)

with phosphorous oxychloride ($POCl_3$) in the presence of a catalyst, wherein each of $R^1$, $R^2$, $R^3$, and $R^4$ is independently H, alkyl, alkenyl, alkynyl, heteroalkyl, aryl, heteroaryl, cycolalkyl, or heterocycloalkyl.

The mole ratio of $POCl_3$ to the compound of Formula (IV) used in the immediate above reaction can be greater than about 100:1, greater than about 50:1, greater than about 10:1, greater than about 8:1, greater than about 6:1, greater than about 5:1, greater than about 4:1, greater than or equal to about 3:1. In a particular embodiment, the mole ratio of $POCl_3$ to the compound of Formula (IV) is greater than or equal to about 3:1. In some embodiments where an excess of the compound of Formula (IV) or $POCl_3$ is used, the excess unreacted reactant can be extracted or separated out with an aqueous basic solution or water.

Similarly, the compound of the formula (IX) can be obtained by reacting the resorcinol spirodichroman compound of Formula (VI):

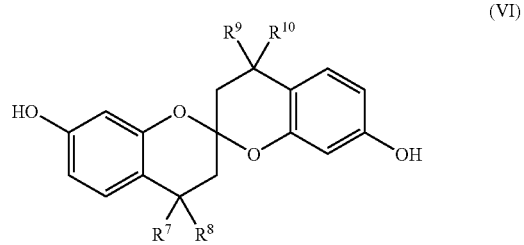

(VI)

with phosphorous oxychloride ($POCl_3$) in the presence of a catalyst or an acid acceptor, wherein each of $R^7$, $R^8$, $R^9$, and $R^{10}$ is independently H, alkyl, alkenyl, alkynyl, heteroalkyl, aryl, heteroaryl, cycolalkyl, or heterocycloalkyl.

The mole ratio of $POCl_3$ to the compound of Formula (VI) used in the immediate above reaction can be greater than about 100:1, greater than about 50:1, greater than about 10:1, greater than about 8:1, greater than about 6:1, greater than about 5:1, greater than about 4:1, greater than about 3:1, greater than or equal to about 2:1. In a particular embodiment, the mole ratio of $POCl_3$ to the compound of Formula (VI) is greater than or equal to about 2:1. In some embodiments where an excess of the compound of Formula (VI) or $POCl_3$ is used, the excess unreacted reactant can be extracted or separated out with an aqueous basic solution or water.

The reaction between Formula (IV) or Formula (VI) and $POCl_3$ can occur in an inert organic solvent such as aromatic hydrocarbons (e.g., toluene, benzene, and xylene), methylene chloride, chloroform, acetonitrile, ethers, and ketones. The preferred solvent is toluene or methylene chloride. In one embodiment, the solvent is methylene chloride. In another embodiment, the solvent is toluene.

Any phosphorylation catalyst known by a person of ordinary skill in the art can be used for the reaction between Formula (IV) or Formula (VI) and POCl$_3$. Non-limiting examples of phosphorylation catalysts include magnesium chloride, aluminum trichloride, titanium tetrachloride, and zinc dichloride. In some embodiments, the solvent for the magnesium chloride-catalyzed phosphorylation is toluene and the reaction temperature is greater than about 35° C., preferably greater than about 55° C., more preferably greater than about 75° C., and most preferably greater than about 100° C. The reaction product can be purified by washing the reaction mixture after completion with water or a basic aqueous solution such as sodium hydroxide solution, sodium carbonate solution, sodium bicarbonate solution, or potassium hydroxide solution. The amount of the catalyst can be in the range from 0.1 wt % to 10 wt % based on the total weight of the reactants. The reaction temperature can be greater than 25° C., greater than 50° C., greater than 75° C., greater than 100° C., greater than 120° C., greater than 140° C., or greater than 150° C.

Any compound that can neutralize hydrogen chloride can be used for the reaction Formula (IV) or Formula (VI) and POCl$_3$. The acid acceptor can be an organic base. Non-limiting examples of suitable organic bases include amines (e.g., trimethylamine, triethylamine, N,N-diisopropylethylamine, triphenylamine, 1,8-diazabicyclo[5.4.0]undec-7-ene), 1-alkylpiperidines such as 1-ethylpiperidine, 1-alkylpyrrolidines such as 1-methylpyrrolidine, pyridine, and combinations thereof. Other suitable amines include, but not limited to, trialkylamines such as tributylamine, trioctylamine, trinonylamine, tridecylamine, triundecylamine, tridodecylamine, tri(tridecyl)amine, tripentadecylamine, trihexadecylamine, triheptadecylamine, trioctadecylamine, trinonadeclyamine, trieicosylamine, tri(tetrachlorododecyl)amine, trihexachloroheptadecylamine, lower alkyl substituted derivatives of pyridine (such as 2,6-lutidine and 2,4,6-collidine), 2,2,6,6-N-pentamethylpiperidine, N,N-dimethylaniline, and diisopropyl-N-ethylamine or combinations thereof. In some embodiments, the acid acceptor is triethylamine. In other embodiments, the solvent for the triethylamine-promoted phosphorylation is methylene chloride and the reaction temperature is less than about 50° C., preferably less than about 35° C., and more preferably between about 20° C. and about 25° C.

Based on the disclosure herein, a person of ordinary skill in the art can recognize that other flavan and spirodichroman phosphate esters, in addition to those represented by Formula (I) and Formula (III), can be obtained from other aromatic compounds having at least two aromatic hydroxy groups such as hydroquinone, 1,2-dihydroxybenzene, 1,2,3-trihydroxybenzene, 1,2,4-trihydroxybenzene, 1,3,5-trihydroxybenzene, bisphenol-A, bisphenol-F, bisphenol-C and biphenols. For example, hydroquinone-based flavan phosphate esters can be obtained according to the scheme below under similar conditions and procedures as disclosed herein for the resorcinol-based flavan phosphate esters.

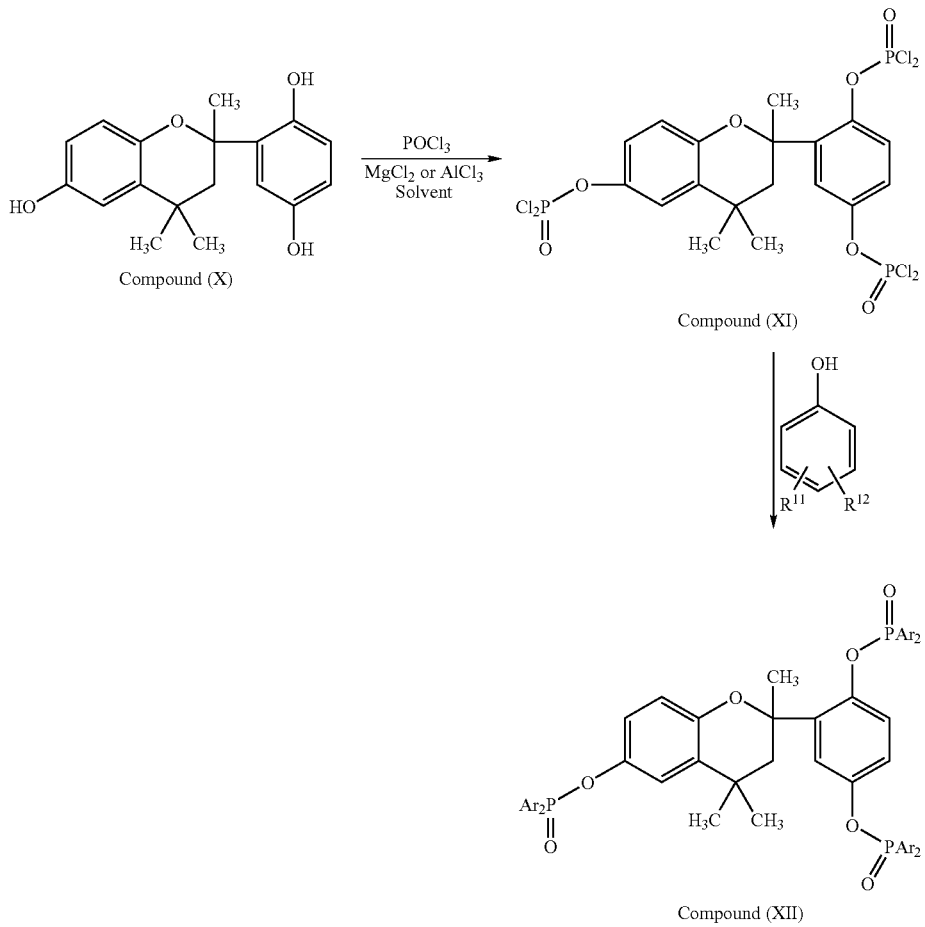

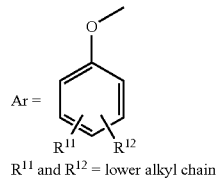

Ar =

$R^{11}$ and $R^{12}$ = lower alkyl chain

Alternatively, hydroquinone-based flavan phosphate esters can be obtained by reacting Compound (X) with Formula (V) in the presence of a catalyst or an acid acceptor under similar conditions and procedures as disclosed herein for the resorcinol-based flavan phosphate esters.

Similarly, hydroquinone-based spirodichroman phosphate esters can be obtained according to the scheme below under similar conditions and procedures as disclosed herein for the resorcinol-based spirodichroman phosphate esters.

Alternatively, hydroquinone-based spirodichroman phosphate esters can be obtained by reacting Compound (XIII) with Formula (V) in the presence of a catalyst or an acid acceptor under similar conditions and procedures as disclosed herein for the resorcinol-based spirodichroman phosphate esters.

The following examples are presented to exemplify embodiments of the invention. All numerical values are approximate. When numerical ranges are given, it should be

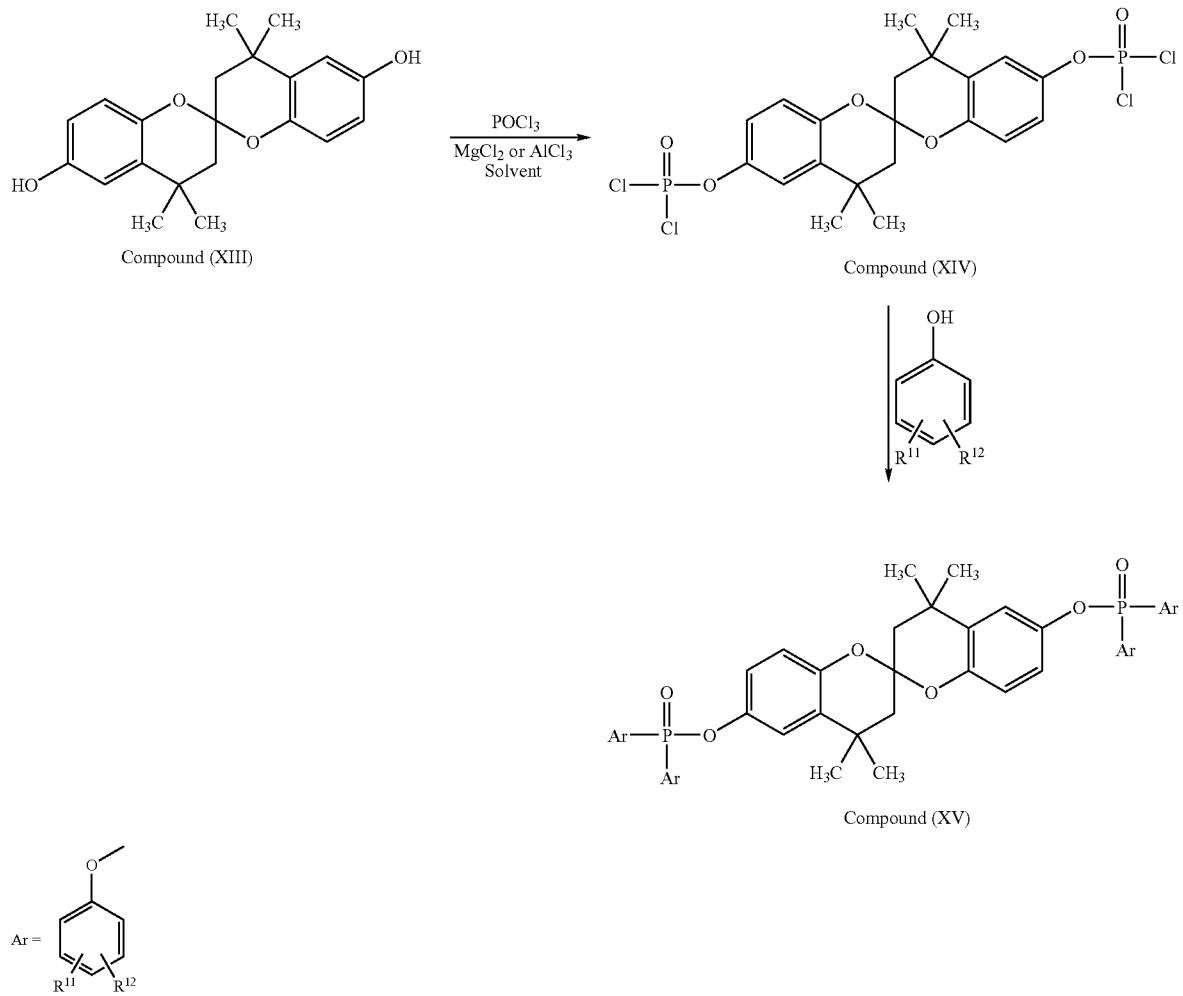

$R^{11}$ and $R^{12}$ = lower alkyl chain understood that embodiments outside the stated ranges may still fall within the scope of the invention. Specific details described in each example should not be construed as necessary features of the invention.

EXAMPLES

Synthesis of Resorcinol Flavan Compound

The reaction of resorcinol with acetone can produce 2,4,4-trimethyl-2',4',7-trihydroxy flavan according to the following reaction scheme.

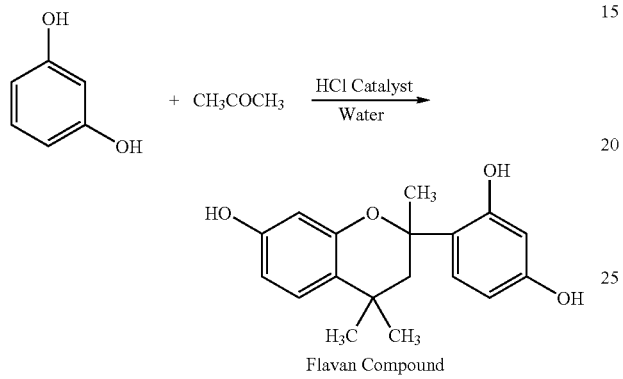

Flavan Compound

A synthetic procedure employed in the preparation of 2,4,4-trimethyl-2',4',7-trihydroxy flavan is outlined below.

Example 1

Resorcinol (1486.5 grams, 13.5 moles), 37% HCl (444 grams, 4.5 moles) and water (1500 ml) were charged into a 5 L round-bottom flask with a mechanical stirrer, thermometer, addition funnel, and reflux condenser. The contents were stirred and heated to 50° C. Acetone (261.5 grams, 4.5 moles) was added drop-wise for 1.5 hrs. The temperature was increased to 60° C. and held for 3 hours. The product was filtered, water washed, and dried, resulting in 609.5 grams of white powder. Analysis indicated 91 (area) % of 2,4,4-trimethyl-2',4',7-trihydroxy flavan compound in the reaction product.

Examples 2-7

Following the synthesis procedure used in Example 1, flavan compounds developed using different molar ratios of resorcinol; acetone, water (solvent) and hydrochloric acid (catalyst) are shown in Table 1.

TABLE 1

| | Ex. 2 | Ex. 3 | Ex. 4 | Ex. 5 | Ex. 6 | Ex. 7 |
|---|---|---|---|---|---|---|
| Reactants | | | | | | |
| Resorcinol (mole) | 1.0 | 1.5 | 4.0 | 8.0 | 10.0 | 0.9 |
| Acetone (mole) | 1.0 | 0.5 | 4.0 | 8.0 | 5.0 | 0.3 |
| 37% HCl (mole) | 0.4 | 0.6 | 1.2 | 3.2 | 1.9 | 0.3 |
| Water (g) | 100 | 240 | 700 | 1400 | 1100 | 100 |
| Reaction Conditions | | | | | | |
| Acetone Addition Temp. (° C.) | 50 | 44 | 49 | 55 | na | 50 |

TABLE 1-continued

| | Ex. 2 | Ex. 3 | Ex. 4 | Ex. 5 | Ex. 6 | Ex. 7 |
|---|---|---|---|---|---|---|
| Reaction Temp. (° C.) | 50 | 44 | 49 | 54 | 20-25 | 50 |
| Product (g) | 110.3 | 34.9 | 337.3 | 721.8 | 531.6 | 17.4 |
| NMR analysis (Area %) | | | | | | |
| Flavan Structure | 73 | 96.3 | 76 | 75 | 93 | 98 | na = Not Applicable

From the results of Examples 2 through 7, higher purity flavan compounds could be synthesized from the resorcinol and acetone reactions. These flavan compounds can be employed directly to synthesize the phosphate ester compounds according to embodiments of the invention.

Synthesis of Phosphate Ester of Resorcinol Flavan Compound

The phosphate ester compound was synthesized using diphenyl chlorophosphate (DPCP) in the reaction, and was based on the following reaction.

Synthesis of Phosphate Ester Using 2,4,4-Trimethyl-2',4',7-trihydroxy Flavan

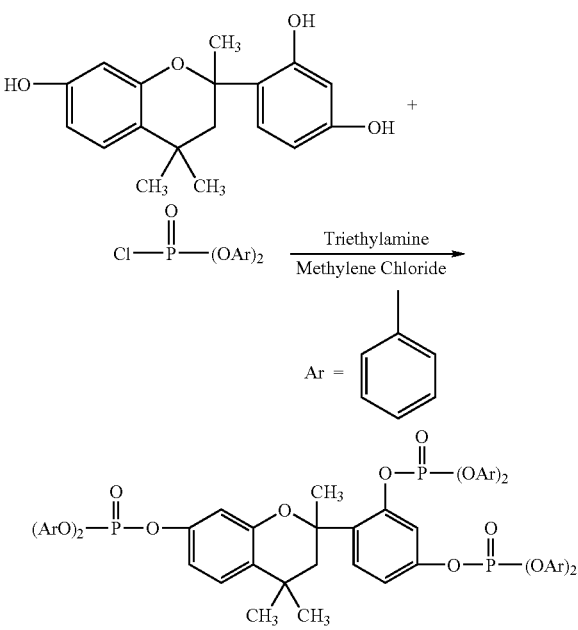

A procedure used in the preparation of flavan based phosphate ester compound is outlined below.

Example 8

The flavan compound of Example 1 (215.0 grams, 0.7 mole), diphenyl chlorophosphate (97.6%; 539.4 grams, 1.96 moles), and methylene chloride (2.0 L) were charged in a 5 L round-bottom flask with a mechanical stirrer, thermometer, addition funnel, reflux condenser with a CaCl$_2$ tube, and heating mantle. The contents were stirred at 35-40° C. A solution of triethylamine (99.5%; 199.3 grams, 1.96 moles) dissolved in methylene chloride (800 ml) was added drop-wise for 2.6 hrs at 35-40° C. The temperature was maintained for an additional 4 hours. The mixture was water washed seven times at 35° C. The methylene chloride was removed at 95° C. using a rotary evaporator (28" Hg vacuum). The product (679.2 grams) was a yellow semi-solid. A $^{13}$C-NMR analysis indicated 82 mole % aromatic C—O—P carbons and 18 mole % (aromatic C—OH carbons+resorcinolic ether carbons), consistent with the desired product. The final phosphate ester material contained 9 weight percent phosphorus.

Examples 10 through 17

Following the synthesis procedures outlined in Examples 8 and 9, the phosphate ester compounds obtained from the flavan compounds have been presented in Examples 10 through 17. The data are summarized in Table 2.

TABLE 2

|  | Ex. 10 | Ex. 11 | Ex. 12 | Ex. 13 | Ex. 14 | Ex. 15 | Ex. 16 | Ex. 17 |
| --- | --- | --- | --- | --- | --- | --- | --- | --- |
| Reactants | | | | | | | | |
| Flavan Compound (mole) | 0.02 | 0.02 | 0.02 | 0.02 | 0.02 | 0.024 | 0.02 | 0.02 |
| Diphenyl chlorophosphate (mole) | 0.06 | 0.06 | 0.06 | 0.06 | 0.072 | 0.048 | 0.056 | 0.06 |
| DPCP/Flavan Compound (mole) | 3 | 3 | 3 | 3 | 3.6 | 2 | 2.8 | 3 |
| Triethylamine (mole) | 0.066 | 0.066 | 0.06 | 0.06 | 0.072 | 0.048 | 0.056 | 0.06 |
| Solvent | Acetone | $CH_2Cl_2$ | $CH_2Cl_2$ | $CH_2Cl_2$ | $CH_2Cl_2$ | $CH_2Cl_2$ | $CH_2Cl_2$ | $CH_2Cl_2$ |
| Reaction Conditions | | | | | | | | |
| Triethylamine Addition Temp. (° C.) | 20-25 | 20-25 | 25/35-40 | 35-40 | 35-40 | 35-40 | 35-40 | 35-40 |
| Triethylamine Addition Time (hr) | 1 | 1.2 | 0.8/.6 | 1.1 | 1 | 1.1 | 1.2 | 1 |
| Reaction Temp. (° C.) | 25/40 | 20-25 | 35-40 | 35-40 | 35-40 | 35-40 | 35-40 | 35-40 |
| Reaction Time (hr) | 1.5/1.5 | 3.5 | 3 | 3 | 3 | 4 | 3.5 | 3.5 |
| Wash | None | Water | W/NaOH/W* | Water | Water | Water | Water | Water |
| Phosphate Ester Product | | | | | | | | |
| Yield (g) | 22.3 | 22.3 | 20.7 | 20.6 | 23.6 | 18.4 | 18.9 | 20 |
| Appearance | Yellow Semi-solid | Pale Yellow Soft solid | Pale Yellow Soft Solid | Pale Yellow Soft Solid | Light Yellow Soft Solid | Tacky White-Grey Solid | Tacky White-Grey Solid | Tacky White-Grey Solid |
| NMR Analysis Results (mole ratio) | | | | | | | | |
| Aromatic C—O—P carbons | 83 | 82 | 83 | 83 | 84 | 72 | 81 | 83 |
| Aromatic C—OH carbons + C—OR (resorcinolic ethers) | 17 | 18 | 17 | 17 | 16 | 28 | 19 | 17 |

*W/NaOH/W means water wash, followed by caustic wash, followed by another water wash product. The product contained 9.1 wt. % phosphorus, had a viscosity of 580 cps at 100° C., and a density of 1.25 at 80° C.

Example 9

The flavan compound of Example 1 (216.5 grams, 0.7 mole), diphenyl chlorophosphate (97.6%; 539.4 grams, 1.96 moles), and methylene chloride (2.0 L) were charged in a 5 L round-bottom flask with a mechanical stirrer, thermometer, addition funnel, reflux condenser with a $CaCl_2$ tube, and heating mantle. The contents were stirred at 35-40° C. A solution of triethylamine (99.5%; 199.3 grams, 1.96 moles) dissolved in methylene chloride (800 ml) was added drop-wise for 2.1 hrs at 35-40° C. The temperature was maintained for an additional 4.2 hours. The mixture was washed at 35° C. with water, 2% NaOH, 0.7% NaOH, and 2 additional water washes. The methylene chloride was removed at 95° C. using a rotary evaporator (28" Hg vacuum). The product (685.9 grams) was a yellow semi-solid. A $^{13}$C-NMR analysis indicated 84 mole % aromatic C—O—P carbons and 16 mole % (aromatic C—OH carbons+resorcinolic ether carbons), consistent with the desired In addition to the low temperature solution method described in Example 8, the high temperature method described below was also employed to synthesize the phosphate ester from the flavan derivative of resorcinol. In this method, the diphenyl chlorophosphate was reacted with the flavan in the presence of magnesium chloride catalyst and heptane solvent as shown below.

Phosphate Ester from Flavan Compound—Magnesium Chloride Catalyst

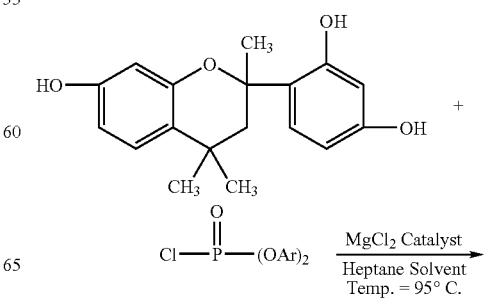

-continued

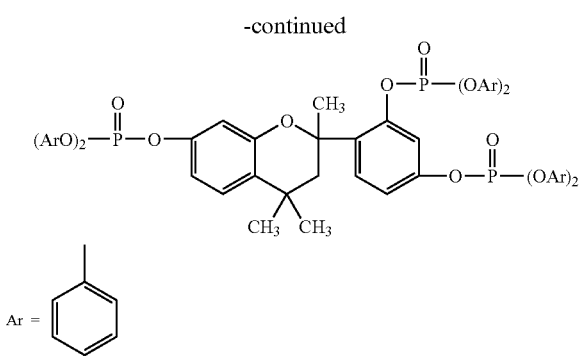

The procedure used in the preparation is outlined below.

Example 18

The flavan compound of Example 1 (6.44 grams, 0.02 moles), diphenyl chlorophosphate (97.6%; 16.5 grams, 0.06 moles), and heptane (30 ml) were charged in a 200 ml round-bottom flask with a mechanical stirrer, thermometer, nitrogen port, reflux condenser, caustic trap, and a heating mantle. The contents were stirred under a $N_2$ sweep for 10 minutes. $MgCl_2$ (0.16 grams) was added to the reaction mixture and the temperature was increased to 95° C. The temperature was maintained at 95° C. until HCl gas evolution stopped (approx. 6.3 hrs). Heptane was removed via distillation. The product (21.4 grams) was a viscous liquid. FT-IR analysis confirmed the following structures were present in the product: hydroxyl, alkyl hydrocarbon, aryl ring, aryl-O, P=O, P—O—C, and monosubstituted benzene ring. A $^{13}$C-NMR analysis indicated 80 mole % aromatic C—O—P carbons and 20 mole % (aromatic C—OH carbons+resorcinolic ether carbons), consistent with the desired product.

In this example, the diphenyl chlorophosphate was added into the reaction mixture containing the flavan compound and triethylamine in the presence of acetone solvent.

Example 19

The flavan compound of Example 1 (6.14 grams, 0.02 mole), triethylamine (99.5%; 5.7 grams, 0.056 moles) and acetone (80 ml) were charged in a 250 ml round-bottom flask with a mechanical stirrer, thermometer, addition funnel, reflux condenser with a $CaCl_2$ tube, and heating mantle. A solution of diphenyl chlorophosphate (97.6%; 15.4 grams, 0.056 moles) dissolved in acetone (40 ml) was added drop-wise for 50 minutes at 55° C. The temperature was maintained at 55° C. for an additional 3.5 hours. The mixture was vacuum filtered to remove the precipitate. Acetone was removed from the organic phase at 95° C. and 28" Hg vacuum. The product was re-dissolved in methylene chloride and washed with water seven times at 35-40° C. The methylene chloride was removed at 95° C. and using a rotary evaporator (28" Hg vacuum). The product (18.4 grams) was a semi-solid material. A $^{13}$C-NMR analysis indicated the product contained 84 mole % aromatic C—O—P carbons and 16 mole % (aromatic C—OH carbons+resorcinolic ether carbons).

Irrespective of the addition order of triethylamine or diphenyl chlorophosphate into the flavan compound, the phosphate ester materials produced contained similar molecular structures based on the NMR analysis.

Example 20

The flavan compound of Example 1 (6.44 grams, 0.02 mole), di(2,6-xylyl) chlorophosphate (326.4 grams/Cl; 19.6 grams, 0.06 moles), and methylene chloride (100 ml) were charged in a 500 ml round-bottom flask with a mechanical stirrer, thermometer, addition funnel, reflux condenser with a $CaCl_2$ tube, and heating mantle. A solution of triethylamine (99.5%; 6.7 grams, 0.066 moles) dissolved in methylene chloride (50 ml) was added drop-wise for 1 hr at 20-25° C. The temperature was maintained for an additional 4 hours. The mixture was washed with water 3 times. The methylene chloride was removed at 90° C. and using a rotary evaporator (28" Hg vacuum), resulting in 27.7 grams of product. A $^{13}$C-NMR analysis indicated the formation of the desired C—O—P bonds and confirmed the formation of phosphate ester structure.

In addition to diphenyl chlorophosphate, phosphorus oxychloride can also be used to synthesize the phosphate ester compound from the resorcinol based flavan derivative obtained in Example 1, and can be based on the following scheme.

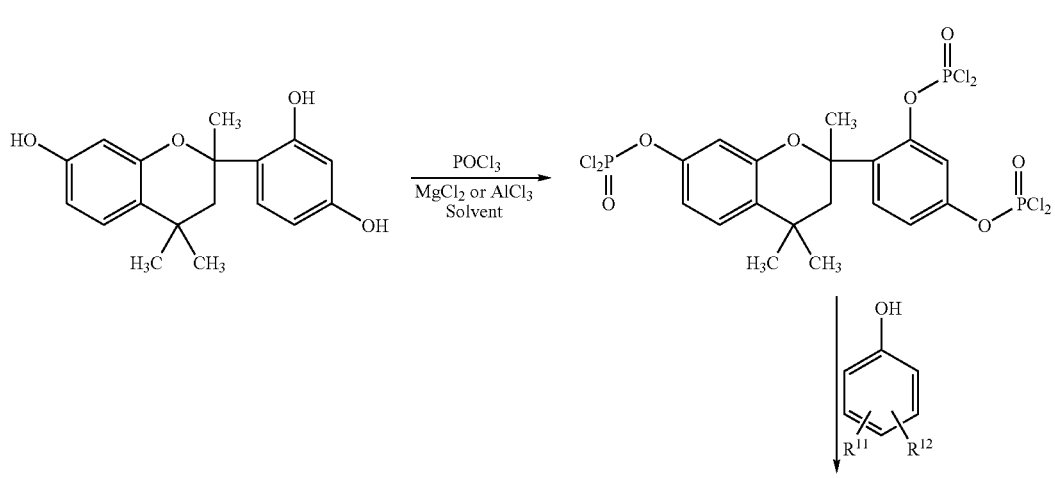

-continued

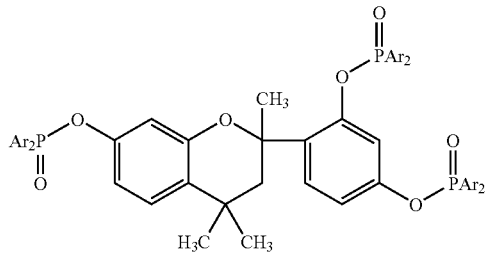

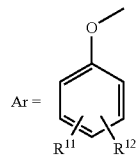

$R^{11}$ and $R^{12}$ = lower alkyl chain

Thermal Stability Data

The thermal stability of phosphate ester compound obtained from the 2,4,4-trimethyl-2',4',7-trihydroxy flavan derivative of Example 8 was determined by thermogravimetric analysis (TGA) under air at a scan rate of 110° C./minute in the temperature range between 25° C. and 700° C. The results are presented in Table 3.

TABLE 3

| Weight Loss: | Temperature (° C.) at Given Weight Loss | | | | |
|---|---|---|---|---|---|
| | 1% | 5% | 10% | 25% | 50% |
| Control (FYROLFLEX ® RDP*) | 248 | 309 | 346 | 383 | 410 |
| Example 8 (A Flavan Based Phosphate Ester) | 238 | 275 | 295 | 333 | 376 |

Note:
*FYROLFLEX ® RDP is a resorcinol diphenylphosphate ester flame retardant available from Akzo Nobel Company.

Polymer Processing and Testing

Example 21

The flame retardant described in Example 9 was added into PC/ABS polymer in a Coperion ZSK-30 twin-screw extruder at two different loadings to provide Examples 21(a) and 21(b), respectively. The PC/ABS blend used was a specially formulated blend that lacks any flame retardant but contains the same PC/ABS terpolymer in commercially available BAYBLEND® FR2010. The skilled artisan will recognize that BAYBLEND® FR2010 (Bayer Material Science, Pittsburgh, Pa.) has a flame retardant incorporated therein. The twin-screw extruder was operated at approximately 55-65 g/min flow rate and the barrel temperature profile was (in direction from feed to nozzle): 190, 240, 240, 245, 250, 257° C. The flame retardant was added using a liquid addition system consisting of a heated reservoir and tubing, Zenith gear pump, and liquid addition nozzle. The liquid addition system was held at 103° C. The flame retardant was added to the extruder at 120 psi through a liquid injection nozzle. The flame retardant-containing pellets were dried and molded into test specimens using an Arburg Allrounder injection molder, with the following temperature profile from feed to nozzle: 243, 253, 258, 265° C. The mold temperature was 190° F. Specimens were conditioned for greater than 40 hrs at 23° C. and 50% humidity. The phosphorus content, heat deflection temperature, melt flow index, notched IZOD impact strength, tensile strength and modulus, flexural modulus, and flammability property were evaluated. The results, along with those of comparative examples (Control 1 and 2), are shown in Table 4.

Comparative Example 1 (Control 1)

Test specimens of commercial BAYBLEND® FR2010 PC/ABS were injection molded as described in Example 21. Heat deflection temperature, melt flow index, IZOD impact strength, tensile, and flexural properties were evaluated for the sample. The results are listed in Table 4.

Comparative Example 2 (Control 2)

The commercial flame retardant FYROLFLEX® RDP (Akzo Nobel Functional Chemicals LLC), resorcinol bis (diphenylphosphate), was added into the specially formulated PC/ABS blend in the twin-screw extruder as was performed in Example 21. Test specimens were then injection molded. Test specimens were then injection molded. The phosphorus contents, heat deflection or distortion temperatures, melt flow indexes, notched IZOD impact strength, tensile strength and moduli, flexural moduli, and flammability properties of Controls 1 and 2 and Examples 21 (a) and 21 (b) were evaluated. The results are shown in Table 4.

The phosphorus content of each of Controls 1 and 2 and Examples 4(a) and 4(b) was measured by the following spectrophotometric technique. A sample was decomposed by treatment with sulfuric acid and nitric acids, and then boiled in a dilute acid to convert phosphate groups in the sample to ortho-phosphate. The ortho-phosphate was complexed with ammonium molybdate and ammonium vanadate in an acid solution. The amount of ortho-phosphate and thus the phosphorus content was measured spectrophotometrically by a Beckman UV/visible spectrophotometer (model DU, from Beckman Coulter, Inc., Fullerton, Calif.) at a wavelength of 470 nm.

The heat deflection temperature at 264 psi fiber stress of each sample was measured by ASTM D648. The melt flow index of each sample was measured by ASTM D1238. The notched IZOD impact strength of each sample was measured by ASTM D256. The tensile strength and modulus of each sample were measured by ASTM D638. The flexural modulus of each sample was measured by ASTM D790. The flammability property of each sample was measured by Underwriters Laboratories UL-94 vertical burn test. All of the above standard tests are incorporated herein by reference.

TABLE 4

| PC/ABS Resin System | Control 1 | Control 2 | Example 21(a) | Example 21(b) |
|---|---|---|---|---|
| Phosphorus Content in PC/ABS (Weight %) | 0.99 | 1.01 | 0.87 | 1.07 |
| Physical Properties | | | | |
| Melt Flow Index (g/10 min.) | 28.6 | 26.1 | 42.6 | 63.6 |
| Heat Distortion Temp. (° C.) | 90.5 | 90.0 | 99.9 | 95.5 |
| Notched Izod (ft-lb/in) | 11.2 | 9.8 | 8.4 | 2.3 |
| Tensile Properties | | | | |
| Strength (MPa) | 58.5 | 57.7 | 56.8 | 57.4 |
| Modulus (GPa) | 2.77 | NA | 2.58 | 2.85 |
| Flexural Property | | | | |
| Modulus (GPa) | 2.83 | 2.78 | 2.58 | 2.66 |
| UL-94 Vertical Burn Test* | | | | |
| Flammability Rating (1/16") | V-0 | V-0 | V-0 | V-2* |
| Total After Flame Time (sec., set of 5 samples) | 16.9 | 9.4 | 4.7 | 13.4 |

Note:
*Upon burning in the UL-94 test, the specimens dripped and ignited the cotton.

The phosphate ester compounds in accordance with embodiments of the invention showed higher melt flow, heat distortion temperatures and better flammability properties at lower phosphorus loading than the control compounds.

Synthesis of Resorcinol Spirochroman Compound

Spirodichroman compound can be synthesized from the reaction of resorcinol with acetone in the presence of an acidic catalyst. With the use of AMBERLYST® 15 catalyst (Aldrich Chemicals, Milwaukee, Wis.), this compound was obtained in good yields, and was based on the following reaction.

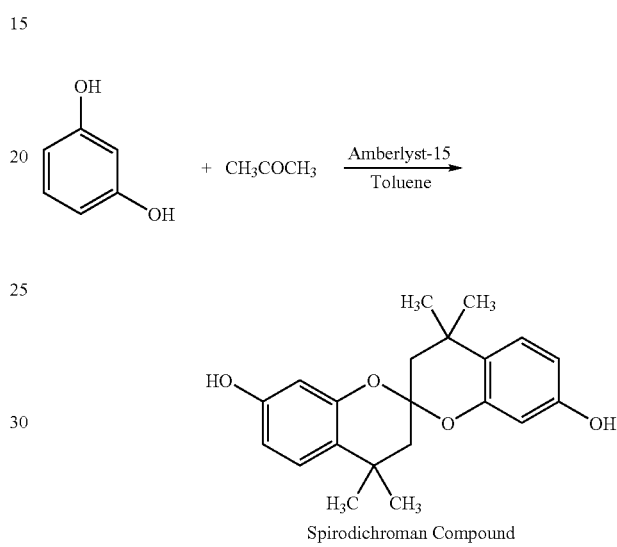

Spirodichroman Compound

The procedure used in the synthesis is given below.

Example 22

Resorcinol (30.0 grams, 0.27 moles), acetone (23.5 grams, 0.405 moles), AMBERLYST® 15 (50 grams), and toluene (300 ml) were charged into a 500 ml 4-neck round bottom flask with a mechanical stirrer, thermometer, and reflux condenser with a $CaCl_2$ tube. The contents were stirred, heated to 85° C., and held for 6.5 hours. The solution was filtered to remove the AMBERLYST® 15. Toluene was removed on a rotary vacuum evaporator at 95° C. and 28" Hg vacuum. The final product (41.8 grams) was a white crystalline powder. A $^{13}C$ NMR analysis indicated structures consistent with the desired product, 89 weight % spirodichroman type structure (shown in Example 24), 7 weight % flavan type structure (shown in Example 1), and 4 weight % unreacted resorcinol.

The spirodichroman compound prepared can be purified and used in the synthesis of the target phosphate ester compound. Using diphenyl chlorophosphate or phosphorus oxychloride as the co-reactant, phosphate esters can be obtained as illustrated below.

Phosphate Ester from Spirodichroman
Compound—POCl₃ Method

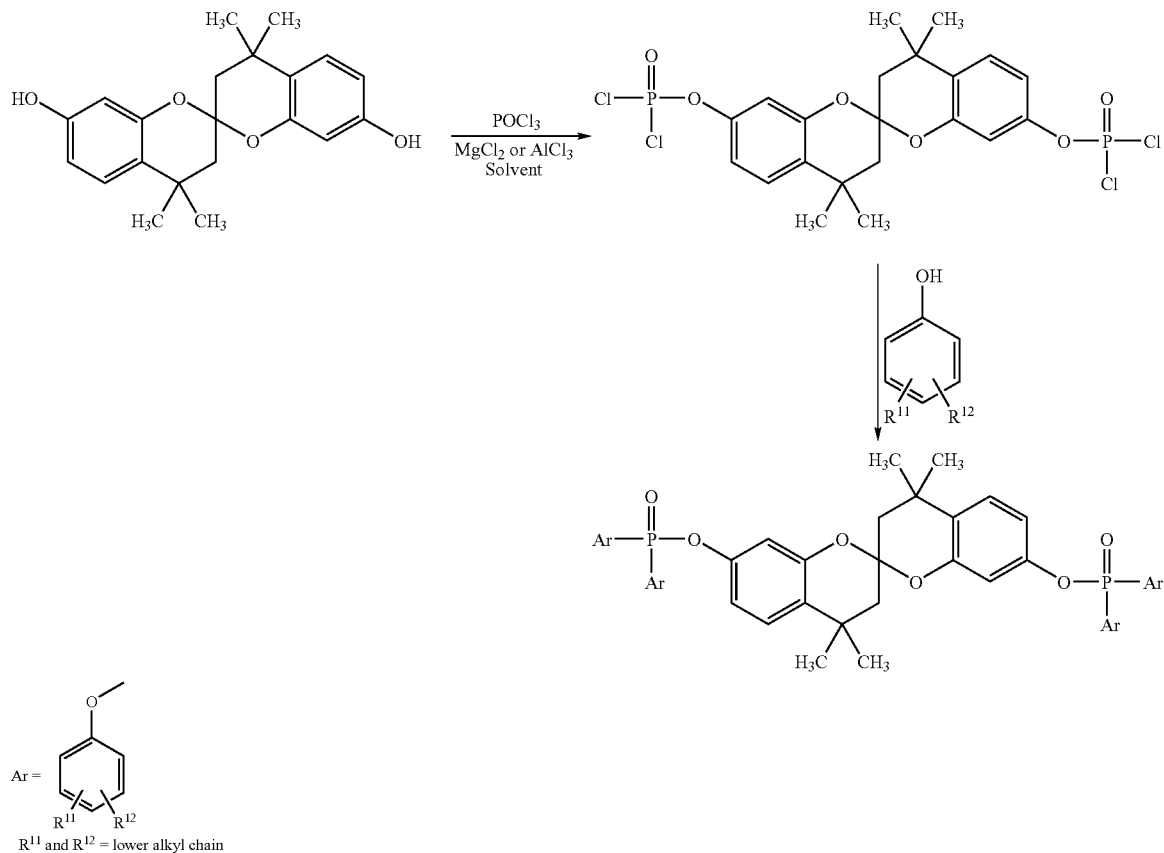

Phosphate Esters from Spirodichroman
Compounds—Diphenylchloro Phosphate Method

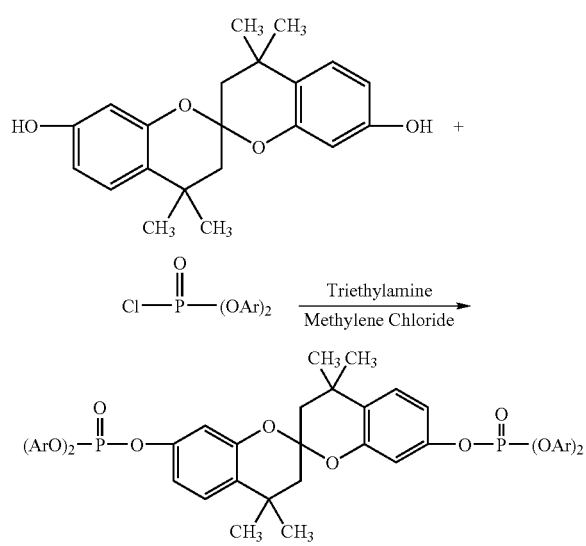

Synthesis of Phosphate Ester of Resorcinol Spirodichroman Compound

The spirodichroman compound obtained from the resorcinol and acetone reaction can be directly used, without isolation, in the synthesis of the corresponding phosphate ester compound. The procedure employed is shown below.

Example 23

Resorcinol (198.2 grams, 1.8 moles), acetone (156.9 grams, 2.7 moles), Amberlyst 15 (330.0 grams), and toluene (1.8 L) were charged into a 4 L resin kettle with a mechanical stirrer, thermometer, and reflux condenser with a CaCl₂ tube. The contents were stirred heated to 85° C. and held for 9.5 hours. The solution was filtered to remove the Amberlyst 15. The organic fractions were returned to the reaction kettle. A Dean-Stark collector was added to the kettle. The reactor contents were heated to reflux and held for 1.5 hr to remove any residual water. The reactor was cooled to room temperature and triethylamine (99.5%; 199.3 grams, 1.96 moles) was added to the kettle. Diphenyl chlorophosphate (97.6%; 539.4 grams, 1.96 moles) dissolved in toluene (360 ml) was added drop-wise at 25-35° C. for 1.1 hr. The contents were heated to 40° C. and held for 4 hr. The contents were transferred to a 5 L 3-neck separatory flask with mechanical stirrer, thermometer, and reflux condenser. The organic phase was washed initially with 400 grams water, followed by a 400 gram wash with 5% NaOH, a 400 gram wash with 2% NaOH, and two additional water washes, all at 40° C. The toluene was removed using a rotary evaporator at 95° C. and 28" Hg vacuum. The product (585.6 grams) was a pale yellow semi-solid material. A $^{13}$C-NMR analysis indicated 47 mole % aromatic phenolic C—O—P carbons, 29 mole % aromatic resorcinolic C—O—P carbons, and 24 mole % aromatic C—O—R aryl ether carbons. No unreacted C—OH carbons were detected. FT-IR analysis indicated the following structures: alkyl and aryl hydrocarbons, aryl-O, P=O, P—O—C, and monosubstituted aromatic structures. The analysis results confirmed the formation of phosphate ester structure proposed in the reaction schemes. The final product showed the phosphorus content of 7.1 weight %.

Thermal Stability Data

The thermal stability of the phosphate ester based on the spirodichroman of Example 23 was determined by TGA method, and the results are presented in Table 5.

TABLE 5

| | Temperature (° C.) at Given Weight Loss | | | | |
|---|---|---|---|---|---|
| Weight Loss: | 1% | 5% | 10% | 25% | 50% |
| Control (FYROLFLEX ® RDP*) | 248 | 309 | 346 | 383 | 410 |
| Example 23 (Spirodichroman-Based Phosphate Ester) | 272 | 352 | 374 | 395 | 411 |

Note:
*FYROLFLEX ® RDP is a resorcinol diphenylphosphate ester flame retardant available from Akzo Nobel Company.

From the Table 5 results, the spirodichroman phosphate ester of Example 23 exhibited higher thermal stability than the resorcinol based phosphate ester (RDP).

Polymer Processing and Testing

Example 24

The flame retardant described in Example 23 was added into the specially formulated PC/ABS blend of Example 21 in a Coperion ZSK-30 twin-screw extruder at two different loadings to provide Examples 24(a) and 24(b), respectively. The twin-screw extruder was operated at approximately 55-65 g/min flow rate and the barrel temperature profile was (in direction from feed to nozzle): 190, 240, 240, 245, 250, 257° C. The flame retardant was added using a liquid addition system consisting of a heated reservoir and tubing, Zenith gear pump, and liquid addition nozzle. The liquid addition system was held at 105° C. The flame retardant was added to the extruder at 120 psi through a liquid injection nozzle. The flame retardant-containing pellets were dried and molded into test specimens using an Arburg Allrounder injection molder, with the following temperature profile from feed to nozzle: 243, 253, 258, 265° C. The mold temperature was 190° F. Specimens were conditioned for greater than 40 hrs at 23° C. and 50% humidity. The results, along with comparative examples (controls 1 and 2), are shown in Table 6.

TABLE 6

| | Control 1 | Control 2 | Example 24(a) | Example 24(b) |
|---|---|---|---|---|
| Phosphorus Content in PC/ABS (Weight %) | 0.99 | 1.01 | 0.96 | 0.75 |
| Physical Properties | | | | |
| Melt Flow Index (g/10 min.) | 28.6 | 26.1 | 37.4 | 31.6 |
| Heat Distortion Temp. (° C.) | 90.5 | 90.0 | 99.8 | 103.6 |
| Notched Izod (ft-lb/in) | 11.2 | 9.8 | 8.2 | 10.2 |
| Tensile Properties | | | | |
| Strength (MPa) | 58.5 | 57.7 | 52.8 | 52.7 |
| Modulus (GPa) | 2.77 | NA | 2.81 | 2.67 |
| Flexural Property | | | | |
| Modulus (GPa) | 2.83 | 2.78 | 2.52 | 2.56 |
| UL-94 Vertical Burn Test* | | | | |
| Flammability Rating (1/16") | V-0 | V-0 | V-2* | V-1 |
| Total After Flame Time (sec., set of 5 samples) | 16.9 | 9.4 | 65.8 | 58.5 |

Note:
*Upon burning in the UL-94 test, the specimens dripped and ignited the cotton.

Based on the above results, the flame retardants in accordance with embodiments of the invention improved the heat distortion temperatures and melt flow properties of the commercially important PC/ABS resin blends. These properties are important for the economical production and applications of PC/ABS and other polymeric materials.

While the invention has been described with respect to a limited number of embodiments, the specific features of one embodiment should not be attributed to other embodiments of the invention. No single embodiment is representative of all aspects of the invention. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. The method of making the flame retardants may be described as comprising a number of acts or steps. These steps or acts may be practiced in any sequence or order unless otherwise indicated. Finally, any number disclosed herein should be construed to mean approximate, regardless of whether the word "about" or "approximately" is used in describing the number. For example, U.S. Pat. Nos. 6,784,234; 6,632,442; 6,630,524; 6,610,765; 6,552,131; 6,448,316; 6,350,804; 6,316,579; 6,204,313; 6,174,942; 6,111,016; 6,083,428; 6,075,158; 5,869,184; 5,864,004; 5,206,281; 5,204,304; and 4,246,169 disclose various compositions and methods that can be used in embodiments of the invention, with or without modifications. As such, all of the above-mentioned patents are incorporated herein by reference in their entirety. The appended claims intend to cover all those modifications and variations as falling within the scope of the invention.

What is claimed is:

1. A flame retardant comprising at least a phosphate ester compound having the formula:

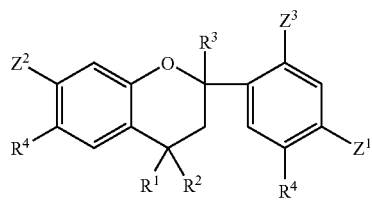

(I)

wherein each of $Z^1$, $Z^2$, and $Z^3$ is independently —OH or a phosphate ester group and at least one of $Z^1$, $Z^2$, and $Z^3$ is a phosphate ester group; and each of $R^1$, $R^2$, $R^3$, and $R^4$ is independently H, alkyl, alkenyl, alkynyl, aryl, cycloalkyl, furyl, thienyl, pyrrolyl, indolyl, indolizinyl, isoindolyl, pyrazolyl, imidazolyl, thiazolyl, thiadiazolyl, benzothiazolyl, 1, 2, 4-triazolyl, 1, 2,3-triazolyl, indazolyl, benzotriazolyl, benzimidazolyl, indazolyl carbazolyl, carbolinyl, benzofuranyl, isobenzofuranyl benzothiophenyl, dibenzofuranyl, dibenzothiophenyl, isothiazolyl, isoxazolyl, pyridyl, purinyl, pyridazinyl, pyrimidinyl, pyrazinyl, triazinyl, tetrazinyl, petazinyl, quinolinyl, isoquinolinyl, perimidinyl, cinnolinyl, phthalazinyl, quinazolinyl, quinoxalinyl, naphthyridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4)dioxinyl, thianthrenyl, or an alkyl group where at least one of the methylene group is replaced by a heteroatom or a hetero-group.

2. The flame retardant of claim 1, wherein the phosphate ester group has the formula:

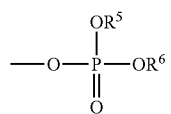

(II)

wherein each of $R^5$ and $R^6$ is independently alkyl, alkenyl, alkynyl, heteroalkyl, aryl, heteroaryl, cycloalkyl, or heterocycloalkyl, or a part of a heterocyclic group when $R^5$ and $R^6$ form the heterocyclic group together with the —O—P(=O)(—O—)—O— fragment; and where each of alkyl, alkenyl, alkynyl, heteroalkyl, aryl, heteroaryl, cycloalkyl, and heterocycloalkyl is substituted or unsubstituted.

3. The flame retardant of claim 2, wherein each of $R^5$ and $R^6$ is independently aryl.

4. The flame retardant of claim 3, wherein each of $R^5$ and $R^6$ is independently phenyl.

5. The flame retardant of claim 1, wherein the phosphate ester group is selected from the group consisting of radicals having the following formulae:

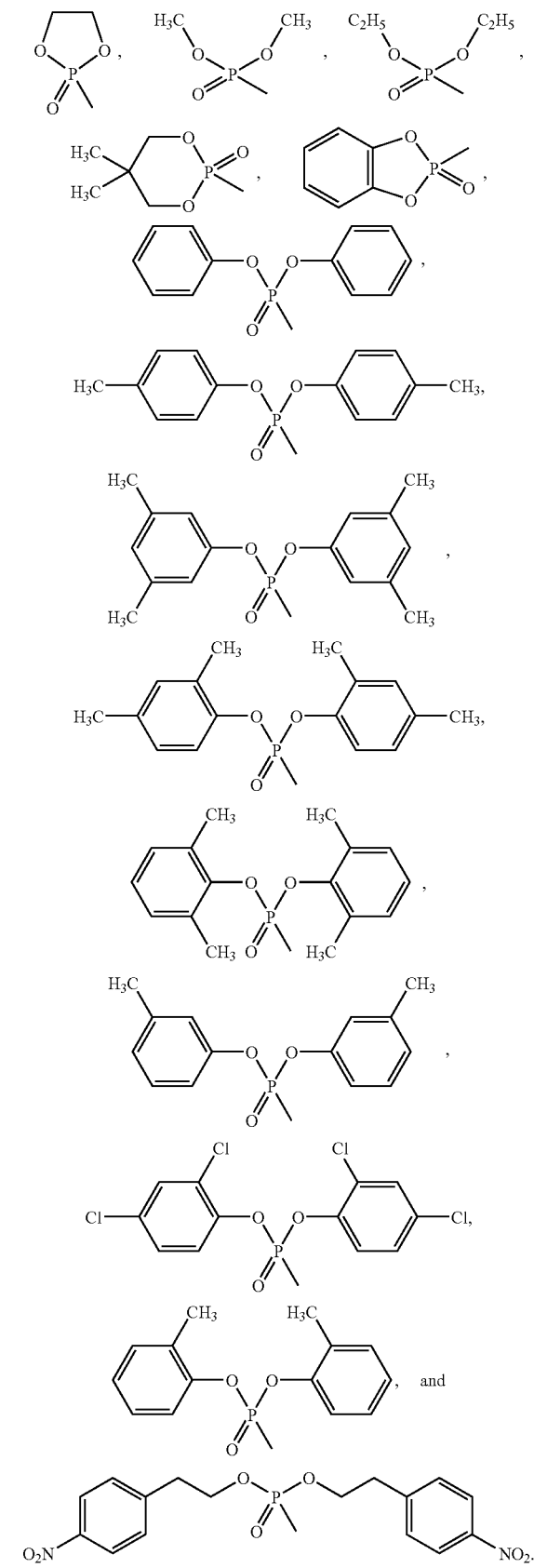

6. A flame retardant comprising at least a phosphate ester compound having the formula:

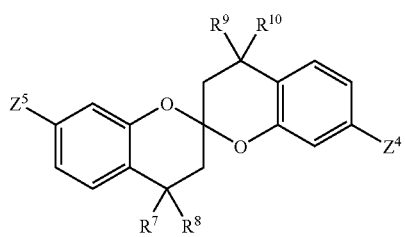
(III)

wherein each of $Z^4$ and $Z^5$ is a phosphate ester group; and each of $R^7$, $R^8$, $R^9$, and $R^{10}$ is independently H, alkyl, alkenyl, alkynyl, aryl, cycloalkyl, furyl, thienyl, pyrrolyl, indolyl, indolizinyl, isoindolyl, pyrazolyl, imidazolyl, thiazolyl, thiadiazolyl, benzothiazoly, 1,2,4-triazolyl, 1,2,3-triazolyl, indazolyl, benzotriazolyl, benzimidazolyl, indazolyl carbazolyl, carbolinyl, benzofuranyl, isobenzofuranyl benzothiophenyl, dibenzofuranyl, dibenzothiophenyl, isothiazolyl, isoxazolyl, pyridyl, purinyl, pyridazinyl, pyrimidinyl, pyrazinyl, triazinyl, tetrazinyl, petazinyl, quinolinyl, isoquinolinyl, perimidinyl, cinnolinyl, phthalazinyl, quinazolinyl, quinoxalinyl, naphthyridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4)dioxinyl, thianthrenyl, or an alkyl group where at least one of the methylene group is replaced by a heteroatom or a hetero-group.

7. The flame retardant of claim 6, wherein the phosphate ester group has the formula:

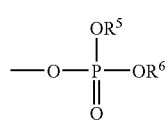
(II)

wherein each of $R^5$ and $R^6$ is independently alkyl, alkenyl, alkynyl, heteroalkyl, aryl, heteroaryl, cycloalkyl, or heterocycloalkyl, or a part of a heterocyclic group when $R^5$ and $R^6$ form the heterocyclic group together with the —O—P(=O)(—O—)—O— fragment; and where each of alkyl, alkenyl, alkynyl, heteroalkyl, aryl, heteroaryl, cycloalkyl, and heterocycloalkyl is substituted or unsubstituted.

8. The flame retardant of claim 7, wherein each of $R^5$ and $R^6$ is independently aryl.

9. The flame retardant of claim 8, wherein each of $R^5$ and $R^6$ is independently phenyl.

10. The flame retardant of claim 6, wherein the phosphate ester group is selected from the group consisting of radicals having the following formulae:

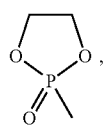 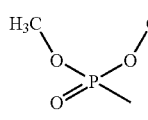 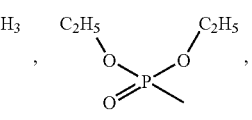

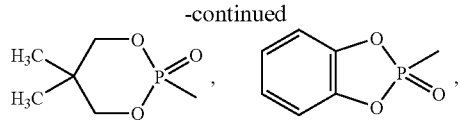

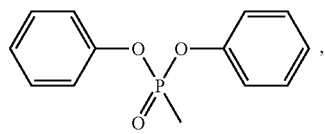

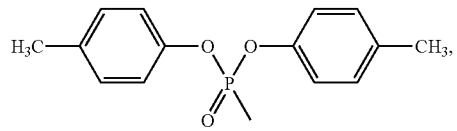

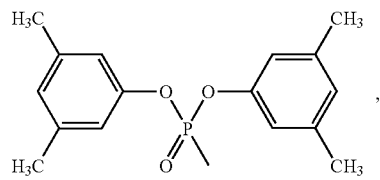

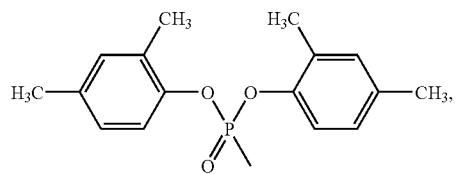

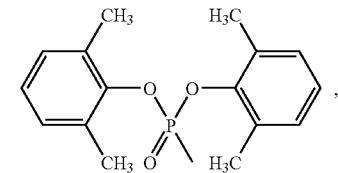

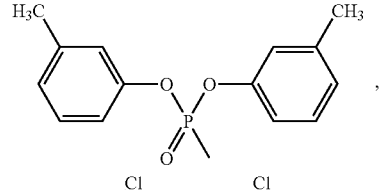

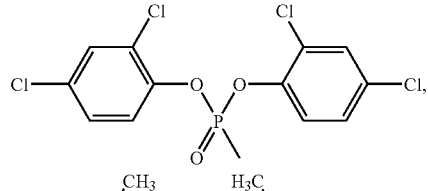

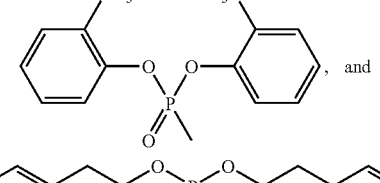

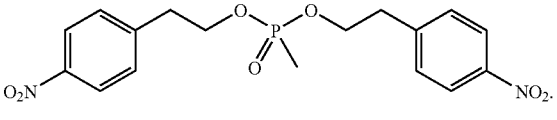

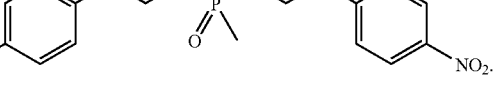

11. A process for preparing a flame retardant comprising at least a phosphate ester compound having the formula:

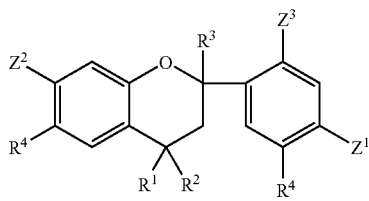
(I)

by reacting a resorcinol flavan compound having the formula:

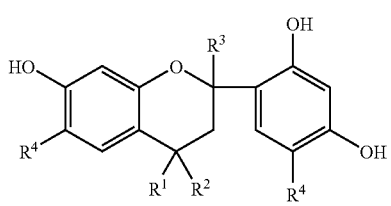
(IV)

with at least a chlorophosphate compound having the formula:

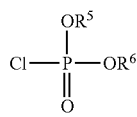
(V)

in the presence of a catalyst or an acid acceptor,
  wherein each of $Z^1$, $Z^2$, and $Z^3$ is independently —OH or a phosphate ester group and at least one of $Z^1$, $Z^2$, and $Z^3$ is a phosphate ester group; and each of $R^1$, $R^2$, $R^3$, and $R^4$ is independently H, alkyl, alkenyl, alkynyl, aryl, cycloalkyl, furyl, thienyl, pyrrolyl, indolyl, indolizinyl, isoindolyl, pyrazolyl, imidazolyl, thiazolyl, thiadiazolyl, benzothiazolyl, 1,2,4-triazolyl, 1,2,3-triazolyl, indazolyl, benzotriazolyl benzimidazolyl, indazolyl carbazolyl, carbolinyl, benzofuranyl, isobenzofuranyl benzothiophenyl, dibenzofuranyl, dibenzothiophenyl, isothiazolyl, isoxazolyl, pyridyl, purinyl, pyridazinyl, pyrimidinyl, pyrazinyl, triazinyl, tetrazinyl, petazinyl, quinolinyl, isoquinolinyl, perimidinyl, cinnolinyl, phthalazinyl, quinazolinyl, quinoxalinyl, naphthyridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo (1,4)dioxinyl, thianthrenyl, or an alkyl group where at least one of the methylene group is replaced by a heteroatom or a hetero-group;
  each of $R^5$ and $R^6$ is independently alkyl, alkenyl, alkynyl, heteroalkyl, aryl, heteroaryl, cycloalkyl, or heterocycloalkyl, or a part of a heterocyclic group when $R^1$ and $R^2$ form the heterocyclic group together with the —O—P(=O)(—Cl—)—O— fragment; and
  where each of alkyl, alkenyl, alkynyl, heteroalkyl, aryl, heteroaryl, cycloalkyl, and heterocycloalkyl is substituted or unsubstituted.

12. The process of claim 11, wherein the reaction occurs in an inert organic solvent.

13. The process of claim 12, wherein the inert organic solvent is selected from the group consisting of heptane, toluene, benzene, xylene, methylene chloride, chloroform, acetonitrile, ethers, ketones, and combinations thereof.

14. The process of claim 11, wherein the catalyst is magnesium chloride, aluminum trichloride, titanium tetrachloride, or zinc dichloride.

15. The process of claim 14, wherein the inert organic solvent is toluene.

16. The process of claim 15, wherein the reaction temperature is greater than 100° C.

17. The process of claim 11, wherein the acid acceptor is an organic base.

18. The process of claim 17, wherein the organic base is triethylamine.

19. The process of claim 18, wherein the inert organic solvent is methylene chloride.

20. The process of claim 19, wherein the reaction temperature is lower than 350° C.

21. A process for preparing a flame retardant comprising at least a phosphate ester compound having the formula:

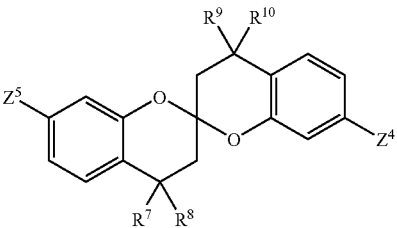
(III)

by reacting a resorcinol spirodichroman compound having the formula:

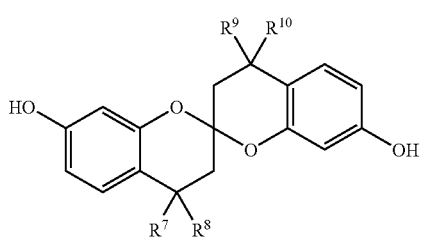
(VI)

with at least a chlorophosphate compound having the formula:

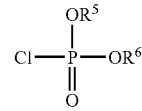
(V)

in the presence of a catalyst or an acid acceptor,
  wherein each of $Z^4$ and $Z^5$ is a phosphate ester group; and each of $R^7$, $R^8$, $R^9$, and $R^{10}$ is H, alkyl, alkenyl, alkynyl, aryl, cycloalkyl, furyl, thienyl, pyrrolyl, indolyl, indolizinyl, isoindolyl, pyrazolyl, imidazolyl, thiazolyl, thiadiazolyl, benzothiazolyl, 1,2,4-triazolyl, 1,2,3-triazolyl, indazolyl, benzotriazolyl, benzimidazolyl, indazolyl carbazolyl, carbolinyl, benzofuranyl, isobenzofuranyl benzothiophenyl, dibenzofuranyl, dibenzothiophenyl, isothiazolyl, isoxazolyl, pyridyl, purinyl, pyridazinyl, pyrimidinyl, pyrazinyl, triazinyl, tetrazinyl, petazinyl, quinolinyl, isoquinolinyl, perimidinyl, cinnolinyl, phthalazinyl, quinazolinyl, quinoxalinyl, naphthyridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4)dioxinyl, thianthrenyl, or an alkyl group where at least one of the methylene group is replaced by a heteroatom or a hetero-group;

each of $R^5$ and $R^6$ is independently alkyl, alkenyl, alkynyl, heteroalkyl, aryl, heteroaryl, cycloalkyl, or heterocycloalkyl, or a part of a heterocyclic group when $R^1$ and $R^2$ form the heterocyclic group together with the —O—P(=O)(—Cl)—O— fragment; and where each of alkyl, alkenyl, alkynyl, heteroalkyl, aryl, heteroaryl, cycloalkyl, and heterocycloalkyl is substituted or unsubstituted.

22. The process of claim 21, wherein the reaction occurs in an inert organic solvent.

23. The process of claim 22, wherein the inert organic solvent is selected from the group consisting of heptane, toluene, benzene, xylene, methylene chloride, chloroform, acetonitrile, ethers, ketones, and combinations thereof.

24. The process of claim 21, wherein the catalyst is magnesium chloride, aluminum trichloride, titanium tetrachloride, or zinc dichloride.

25. The process of claim 24, wherein the inert organic solvent is toluene.

26. The process of claim 25, wherein the reaction temperature is greater than 100° C.

27. The process of claim 21, wherein the acid acceptor is an organic base.

28. The process of claim 27, wherein the organic base is triethylamine.

29. The process of claim 28, wherein the inert organic solvent is methylene chloride.

30. The process of claim 29, wherein the reaction temperature is lower than 35° C.

31. A process for preparing the flame retardant of claim 2, comprising the step of reacting a compound of the formula:

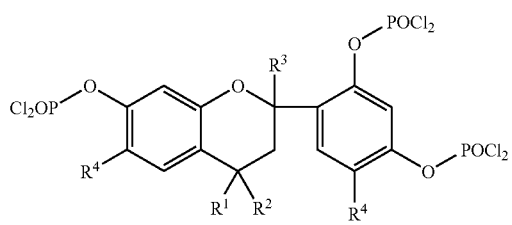

(VII)

with at least one hydroxyl compound in the presence of a catalyst.

32. The process of claim 31, wherein the compound of formula (VII) is prepared by reacting a compound of the formula:

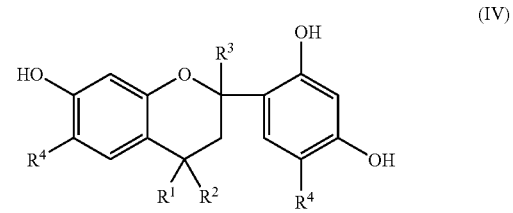

(IV)

wherein each of $R^1$, $R^2$, $R^3$, and $R^4$ is independently H, alkyl, alkenyl, alknyl, aryl, cycloalkyl, furyl, thienyl, pyrrolyl, indolyl, indolizinyl, isoindolyl, pyrazolyl, imidazolyl, thiazolyl, thiadiazolyl, benzothiazolyl, 1,2,4-triazolyl, 1,2,3-triazolyl, indazolyl, benzotriazolyl, benzimidazolyl, indazolyl carbazolyl, carbolinyl, benzofuranyl, isobenzofuranyl benzothiophenyl, dibenzofuranyl, dibenzothiophenyl, isothiazolyl, isoxazolyl, pyridyl, purinyl, pyridazinyl, pyrimidinyl, pyrazinyl, triazinyl, tetrazinyl, petazinyl, quinolinyl, isoquinolinyl, perimidinyl, cinnolinyl, phthalazinyl, quinazolinyl, quinoxalinyl, naphthyridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4)dioxinyl, thianthrenyl, or an alkyl group where at least one of the methylene group is replaced by a heteroatom or a hetero-group;

with phosphorous oxychloride in the presence of a catalyst.

33. The process of claim 32, wherein the reaction occurs in an inert organic solvent.

34. The process of claim 32, wherein the catalyst is an organic base selected from the group consisting of amines, 1-alkylpiperidines, 1alkylpyrrolidines, pyridine, imidazole, and combinations thereof.

35. The process of claim 32, wherein the catalyst is magnesium chloride, aluminum trichloride, titanium tetrachloride, or zinc dichloride.

36. The process of claim 31, wherein each of $R^5$ and $R^6$ is independently aryl.

37. The process of claim 36, wherein each of $R^5$ and $R^6$ is independently phenyl.

38. A process for preparing the flame retardant of claim 7, comprising the step of reacting a compound of the formula:

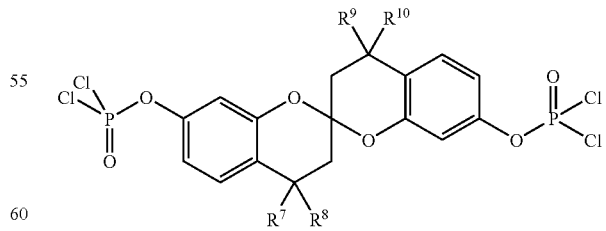

(IX)

with at least one hydroxyl compound in the presence of a catalyst.

39. The process of claim 31, wherein the compound of formula (IX) is prepared by reacting a compound of the formula:

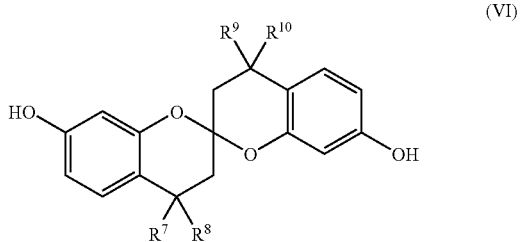

(VI)

wherein each of $R^7$, $R^8$, $R^9$, and $R^{10}$ is independently H, alkyl, alkenyl, alkynyl, aryl, cycloalkyl, furyl, thienyl, pyrrolyl, indolyl, indolizinyl, isoindolyl, pyrazolyl, imidazolyl, thiazolyl, thiadiazolyl, benzothiazolyl, 1,2,4-triazolyl, 1,2,3-triazolyl, indazolyl, benzotriazolyl, benzimidazolyl, indazolyl carbazolyl, carbolinyl, benzofuranyl, isobenzofuranyl benzothiophenyl, dibenzofuranyl, dibenzothiophenyl, isothiazolyl, isoxazolyl, pyridyl, purinyl, pyridazinyl, pyrimidinyl, pyrazinyl, triazinyl, tetrazinyl, petazinyl, quinolinyl, isoquinolinyl, perimidinyl, cinnolinyl, phthalazinyl, quinazolinyl, quinoxalinyl, naphthyridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4)dioxinyl, thianthrenyl, or an alkyl group where at least one of the methylene group is replaced by a heteroatom or a hetero-group; with phosphorous oxychloride in the presence of a catalyst.

40. The process of claim 39, wherein the reaction occurs in an inert organic solvent.

41. The process of claim 39, wherein the catalyst is an organic base selected from the group consisting of amines, 1-alkylpiperidines, 1-alkylpyrrolidines, pyridine, imidazole, and combinations thereof.

42. The process of claim 39, wherein the catalyst is magnesium chloride, aluminum trichloride, titanium tetrachloride, or zinc dichloride.

43. The process of claim 36, wherein each of $R^5$ and $R^6$ is independently aryl.

44. The process of claim 43, wherein each of $R^5$ and $R^6$ is independently phenyl.

45. A flame retardant composition comprising a polymer and a flame retardant of claim 1 or 6.

46. The flame retardant composition of claim 45, wherein the polymer is selected from the group consisting of polycarbonates, poly(phenylene oxide), polyarylates, polymethacrylates, polyesters, acrylonitrile-butadiene-styrene terpolymer, high-impact polystyrene, and combinations or blends thereof.

47. The flame retardant composition of claim 45, further comprising at least an additive selected from the group consisting of extenders, fibers, fillers, coupling agents, cross-linking agents, plasticizers, impact modifiers, compatibilizers, anti-blocking agents, anti-fogging agents, anti-aging agent, antioxidants, UV stabilizers, antiozonants, acid scavengers, processing aids, surfactants, lubricants, plasticizing agents, parting agents and abherents, nucleating agents, anti-static agents, slip agents, chemical blowing agents, fluorescent whitening agents, flow agents, deodorants, release agents, colorants, and anti-microbials.

48. The flame retardant composition of claim 45, wherein the flame retardant composition is substantially free of an additive.

49. An article comprising a flame retardant composition of claim 45.

50. The article of claim 49, wherein the article is selected from the group consisting of plastic products, textiles, wood and paper products, adhesives and sealants, and rubber products, aerospace parts, automotive parts, wires, cables, construction materials, materials for interiors and furnishings, appliances, electronic components, computers, and business machines.

51. The article of claim 49, wherein the polymer is selected from the group consisting of polycarbonates, poly(phenylene oxide), polyarylates, polymethacrylates, polyesters, acrylonitrile-butadiene-styrene terpolymer, high-impact polystyrene, and combinations or blends thereof.

52. The article of claim 49, wherein the flame retardant composition further comprises at least an additive selected from the group consisting of extenders, fibers, fillers, coupling agents, cross-linking agents, plasticizers, impact modifiers, compatibilizers, anti-blocking agents, anti-fogging agents, anti-aging agents, antioxidants, UV stabilizers, antiozonants, acid scavengers, processing aids, surfactants, lubricants, plasticizing agents, parting agents and abherents, nucleating agents, anti-static agents, slip agents, chemical blowing agents, fluorescent whitening agents, flow agents, deodorants, release agents, colorants, and anti-microbials.

53. The article of claim 49, wherein the flame retardant composition is substantially free of an additive.

* * * * *

UNITED STATES PATENT AND TRADEMARK OFFICE
CERTIFICATE OF CORRECTION

PATENT NO. : 7,365,113 B2
APPLICATION NO. : 11/233586
DATED : April 29, 2008
INVENTOR(S) : Durairaj et al.

It is certified that error appears in the above-identified patent and that said Letters Patent is hereby corrected as shown below:

In column 37, line 20, delete "benzothiazoly," and insert -- benzothiazolyl, --.

In column 39, line 64, delete "-O-P(=O)(-Cl-)-O-" and insert -- -O-P(=O)(-Cl)-O- --.

In column 40, line 21, delete "350°C" and insert -- 35°C --.

In column 41, line 32, delete "chioride" and insert -- chloride --.

In column 42, line 37, delete "1alkylpyrrolidines" and insert -- 1-alkylpyrrolidines --.

In column 44, line 11, delete "scavangers" and insert -- scavengers --.

Signed and Sealed this

Seventh Day of April, 2009

JOHN DOLL
*Acting Director of the United States Patent and Trademark Office*